United States Patent
Forsell

(10) Patent No.: US 9,370,656 B2
(45) Date of Patent: Jun. 21, 2016

(54) SYSTEM, AN APPARATUS, AND A METHOD FOR TREATING A SEXUAL DYSFUNCTIONAL FEMALE PATIENT

(71) Applicant: Peter Forsell, Bouveret (CH)

(72) Inventor: Peter Forsell, Bouveret (CH)

( * ) Notice: Subject to any disclaimer, the term of this patent is extended or adjusted under 35 U.S.C. 154(b) by 0 days.

(21) Appl. No.: 14/467,849

(22) Filed: Aug. 25, 2014

(65) Prior Publication Data

US 2015/0165197 A1    Jun. 18, 2015

Related U.S. Application Data

(63) Continuation of application No. 13/123,145, filed as application No. PCT/SE2009/051127 on Oct. 9, 2009, now Pat. No. 8,874,215.

(30) Foreign Application Priority Data

Oct. 10, 2008   (SE) ...................................... 0802162

(51) Int. Cl.
*A61N 1/00*   (2006.01)
*A61N 1/36*   (2006.01)
*A61N 1/05*   (2006.01)
*A61H 19/00*  (2006.01)

(52) U.S. Cl.
CPC ............ *A61N 1/36007* (2013.01); *A61H 19/34* (2013.01); *A61N 1/0524* (2013.01); *A61N 1/36107* (2013.01)

(58) Field of Classification Search
CPC ............ A61N 1/36; A61N 1/18; A61B 5/05; A61K 31/00
See application file for complete search history.

(56) References Cited

U.S. PATENT DOCUMENTS

| | | |
|---|---|---|
| 2,060,913 A | 11/1936 | Weaver |
| 2,795,641 A | 6/1957 | Rowell |
| 3,209,081 A | 9/1965 | Ducote et al. |
| 3,357,432 A | 12/1967 | Sparks |
| 3,598,287 A | 8/1971 | De Man |
| 3,626,931 A | 12/1971 | Bysakh |
| 3,662,758 A | 5/1972 | Glover |
| 3,692,027 A | 9/1972 | Ellinwood, Jr. |
| 3,705,575 A | 12/1972 | Edwards |
| 3,731,679 A | 5/1973 | Wilhelmson et al. |
| 3,731,681 A | 5/1973 | Blackshear et al. |
| 3,750,194 A | 8/1973 | Summers |

(Continued)

FOREIGN PATENT DOCUMENTS

| | | |
|---|---|---|
| CN | 104 74 47 | 12/1990 |
| CN | 227 58 59 | 3/1998 |

(Continued)

OTHER PUBLICATIONS

U.S. Appl. No. 09/373,224, filed Aug. 12, 1999, Forsell.

(Continued)

*Primary Examiner* — Robert N Wieland

(57) ABSTRACT

There is disclosed an apparatus for treating a sexual dysfunctional female patient, comprising a stimulation device adapted to stimulate an erectile blood flow passageway to increase the amount of blood in the female erectile tissue and thereby obtaining engorgement with blood of the female erectile tissue by affecting said erectile blood flow passageway. Moreover there is disclosed a system and an operation method for treating a sexual dysfunctional female patient.

20 Claims, 11 Drawing Sheets

(56) References Cited

U.S. PATENT DOCUMENTS

| | | |
|---|---|---|
| 3,817,237 A | 6/1974 | Bolduc |
| 3,855,122 A | 12/1974 | Bourganel |
| 3,863,622 A | 2/1975 | Buuck |
| 3,875,928 A | 4/1975 | Angelchik |
| 3,906,674 A | 9/1975 | Stone |
| 3,923,060 A | 12/1975 | Ellinwood, Jr. |
| 3,926,195 A | 12/1975 | Bleier et al. |
| 3,954,102 A | 5/1976 | Buuck |
| 4,003,379 A | 1/1977 | Ellinwood, Jr. |
| 4,009,711 A | 3/1977 | Uson |
| 4,026,305 A | 5/1977 | Brownlee et al. |
| 4,044,401 A | 8/1977 | Guiset |
| 4,050,449 A | 9/1977 | Castellana et al. |
| 4,146,029 A | 3/1979 | Ellinwood, Jr. |
| 4,153,059 A | 5/1979 | Fravel et al. |
| 4,190,040 A | 2/1980 | Schulte |
| 4,201,202 A | 5/1980 | Finney et al. |
| 4,221,219 A | 9/1980 | Tucker |
| 4,235,222 A | 11/1980 | Ionescu |
| 4,243,306 A | 1/1981 | Bonini |
| 4,245,623 A | 1/1981 | Erb |
| 4,246,893 A | 1/1981 | Berson |
| 4,265,241 A | 5/1981 | Portner et al. |
| 4,271,827 A | 6/1981 | Angelchik |
| 4,274,407 A | 6/1981 | Scarlett |
| 4,304,225 A | 12/1981 | Freeman |
| 4,318,396 A | 3/1982 | Finney |
| 4,342,308 A | 8/1982 | Trick |
| 4,369,771 A | 1/1983 | Trick |
| 4,400,169 A | 8/1983 | Stephens |
| 4,408,597 A | 10/1983 | Tenney, Jr. |
| 4,412,530 A | 11/1983 | Burton |
| 4,424,807 A | 1/1984 | Evans |
| 4,505,710 A | 3/1985 | Collins |
| 4,509,947 A | 4/1985 | Lattin |
| 4,538,607 A | 9/1985 | Saul |
| 4,542,753 A | 9/1985 | Brenman et al. |
| 4,550,720 A | 11/1985 | Trick |
| 4,556,050 A | 12/1985 | Hodgson et al. |
| 4,559,930 A | 12/1985 | Cobiski |
| 4,559,931 A | 12/1985 | Fischell |
| 4,563,175 A | 1/1986 | La Fond |
| 4,568,851 A | 2/1986 | Soni et al. |
| 4,580,578 A | 4/1986 | Barsom |
| 4,583,523 A | 4/1986 | Kleinke et al. |
| 4,584,994 A | 4/1986 | Bamberger et al. |
| 4,587,954 A | 5/1986 | Haber |
| 4,592,339 A | 6/1986 | Kuzmak et al. |
| 4,592,355 A | 6/1986 | Antebi |
| 4,599,081 A | 7/1986 | Cohen |
| 4,602,621 A | 7/1986 | Hakky |
| 4,610,658 A | 9/1986 | Buchwald et al. |
| 4,623,350 A | 11/1986 | Lapeyre et al. |
| 4,628,928 A | 12/1986 | Lowell |
| 4,634,443 A | 1/1987 | Haber |
| 4,664,100 A | 5/1987 | Rudloff |
| 4,677,534 A | 6/1987 | Okochi |
| 4,679,560 A | 7/1987 | Galbraith |
| 4,696,288 A | 9/1987 | Kuzmak et al. |
| 4,711,231 A | 12/1987 | Finegold et al. |
| 4,723,538 A | 2/1988 | Stewart et al. |
| 4,728,328 A | 3/1988 | Hughes et al. |
| 4,756,949 A | 7/1988 | Spence et al. |
| 4,771,772 A | 9/1988 | DeWitt |
| 4,771,780 A | 9/1988 | Sholder |
| 4,773,403 A | 9/1988 | Daly |
| 4,780,064 A | 10/1988 | Olsen |
| 4,786,276 A | 11/1988 | Haber |
| 4,822,341 A | 4/1989 | Colone |
| 4,828,544 A | 5/1989 | Lane et al. |
| 4,828,990 A | 5/1989 | Higashi et al. |
| 4,829,990 A | 5/1989 | Thuroff et al. |
| 4,846,794 A | 7/1989 | Hertzer |
| 4,878,889 A | 11/1989 | Polyak |
| 4,902,279 A | 2/1990 | Schmidtz et al. |
| 4,925,443 A | 5/1990 | Heilman et al. |
| 4,941,461 A | 7/1990 | Fischell |
| 4,942,668 A | 7/1990 | Franklin |
| 4,950,224 A | 8/1990 | Gorsuch et al. |
| 4,958,630 A | 9/1990 | Rosenbluth et al. |
| 4,979,955 A | 12/1990 | Smith |
| 4,982,731 A | 1/1991 | Lue et al. |
| 4,983,177 A | 1/1991 | Wolf |
| 5,006,106 A | 4/1991 | Angelchik |
| 5,012,822 A | 5/1991 | Schwarz |
| 5,042,084 A | 8/1991 | Daly |
| 5,048,511 A | 9/1991 | Rosenbluth et al. |
| 5,057,075 A | 10/1991 | Moncrief et al. |
| 5,062,416 A | 11/1991 | Stucks |
| 5,074,868 A | 12/1991 | Kuzmak |
| 5,078,676 A | 1/1992 | Bailly |
| 5,098,369 A | 3/1992 | Heilman et al. |
| 5,112,202 A | 5/1992 | Oshima et al. |
| 5,123,428 A | 6/1992 | Schwarz |
| 5,151,082 A | 9/1992 | Gorsuch et al. |
| 5,152,743 A | 10/1992 | Gorsuch et al. |
| 5,160,338 A | 11/1992 | Vincent |
| 5,194,145 A | 3/1993 | Schoendorfer |
| 5,224,926 A | 7/1993 | Gorsuch et al. |
| 5,226,429 A | 7/1993 | Kuzmak |
| 5,250,020 A | 10/1993 | Bley |
| 5,261,898 A | 11/1993 | Polin et al. |
| 5,272,664 A | 12/1993 | Alexander et al. |
| 5,297,536 A | 3/1994 | Wilk |
| 5,304,206 A | 4/1994 | Baker, Jr. et al. |
| 5,316,543 A | 5/1994 | Eberbach |
| 5,324,263 A | 6/1994 | Kraus et al. |
| 5,352,183 A | 10/1994 | Jonsson et al. |
| 5,358,474 A | 10/1994 | Kaldany |
| 5,397,354 A | 3/1995 | Wilk et al. |
| 5,415,660 A | 5/1995 | Campbell et al. |
| 5,435,230 A | 7/1995 | Phillips |
| 5,437,605 A | 8/1995 | Helmy |
| 5,449,368 A | 9/1995 | Kuzmak |
| 5,453,079 A | 9/1995 | Schwaninger |
| 5,454,840 A | 10/1995 | Krakovsky et al. |
| 5,501,703 A | 3/1996 | Holsheimer et al. |
| 5,504,700 A | 4/1996 | Insley et al. |
| 5,505,733 A | 4/1996 | Justin et al. |
| 5,509,888 A | 4/1996 | Miller |
| 5,518,499 A | 5/1996 | Aghr |
| 5,518,504 A | 5/1996 | Polyak |
| 5,531,684 A | 7/1996 | Ensminger et al. |
| 5,540,731 A | 7/1996 | Testerman |
| 5,569,187 A | 10/1996 | Kaiser |
| 5,578,069 A | 11/1996 | Miner, II |
| 5,582,580 A | 12/1996 | Buckman, Jr. et al. |
| 5,632,753 A | 5/1997 | Loeser |
| 5,665,065 A | 9/1997 | Colman et al. |
| 5,676,674 A | 10/1997 | Bolanos et al. |
| 5,690,108 A | 11/1997 | Chakeres |
| 5,690,691 A | 11/1997 | Chen et al. |
| 5,702,431 A | 12/1997 | Wang et al. |
| 5,704,893 A | 1/1998 | Timm |
| 5,704,915 A | 1/1998 | Melsky et al. |
| 5,735,809 A | 4/1998 | Gorsuch |
| 5,735,887 A | 4/1998 | Barreras et al. |
| 5,738,792 A | 4/1998 | Schoendorfer |
| 5,749,909 A | 5/1998 | Schroeppel et al. |
| 5,769,877 A | 6/1998 | Barreras |
| 5,771,903 A | 6/1998 | Jakobsson |
| 5,814,020 A | 9/1998 | Gross |
| 5,823,991 A | 10/1998 | Shim |
| 5,827,286 A | 10/1998 | Incavo et al. |
| 5,836,935 A | 11/1998 | Ashton et al. |
| 5,848,962 A | 12/1998 | Feindt et al. |
| 5,858,001 A | 1/1999 | Tsals et al. |
| 5,876,425 A | 3/1999 | Gord et al. |
| 5,900,909 A | 5/1999 | Parulski et al. |
| 5,902,336 A | 5/1999 | Mishkin |
| 5,910,149 A | 6/1999 | Kuzmak |
| 5,928,195 A | 7/1999 | Malamud et al. |
| 5,938,584 A | 8/1999 | Ardito et al. |
| 5,938,669 A | 8/1999 | Klaiber et al. |

(56) References Cited

U.S. PATENT DOCUMENTS

| | | |
|---|---|---|
| 5,954,715 A | 9/1999 | Harrington et al. |
| 5,964,789 A | 10/1999 | Karsdon |
| 5,978,712 A | 11/1999 | Suda et al. |
| 5,980,478 A | 11/1999 | Gorsuch et al. |
| 5,995,874 A | 11/1999 | Borza |
| 5,997,501 A | 12/1999 | Gross et al. |
| 6,003,736 A | 12/1999 | Ljunggren |
| 6,034,878 A | 3/2000 | Umemura et al. |
| 6,039,748 A | 3/2000 | Savage et al. |
| 6,050,982 A | 4/2000 | Wheeler |
| 6,067,991 A | 5/2000 | Forsell |
| 6,074,341 A | 6/2000 | Anderson et al. |
| 6,077,215 A | 6/2000 | Leysieffer |
| 6,095,968 A | 8/2000 | Snyders |
| 6,099,460 A | 8/2000 | Denker |
| 6,102,887 A | 8/2000 | Altman |
| 6,102,922 A | 8/2000 | Jakobsson et al. |
| 6,113,574 A | 9/2000 | Spinello |
| 6,116,193 A | 9/2000 | Goeckner |
| 6,117,067 A | 9/2000 | Gil-Vernet |
| 6,134,470 A | 10/2000 | Hartlaub |
| 6,135,945 A | 10/2000 | Sultan |
| 6,145,505 A | 11/2000 | Nikolchev et al. |
| 6,162,238 A | 12/2000 | Kaplan et al. |
| 6,170,484 B1 | 1/2001 | Feng |
| 6,185,452 B1 | 2/2001 | Schulman et al. |
| 6,197,055 B1 | 3/2001 | Matthews |
| 6,210,347 B1 | 4/2001 | Forsell |
| 6,215,727 B1 | 4/2001 | Parson |
| 6,221,060 B1 | 4/2001 | Willard |
| 6,233,474 B1 | 5/2001 | Lemelsom |
| 6,266,560 B1 | 7/2001 | Zhang et al. |
| 6,275,737 B1 | 8/2001 | Mann |
| 6,302,910 B1 | 10/2001 | Yamazaki et al. |
| 6,319,191 B1 | 11/2001 | Sayet et al. |
| 6,321,282 B1 | 11/2001 | Horowitz |
| 6,332,466 B1 | 12/2001 | Yoon |
| 6,346,099 B1 | 2/2002 | Altman |
| 6,377,640 B2 | 4/2002 | Trans |
| 6,402,767 B1 | 6/2002 | Nash et al. |
| 6,436,054 B1 | 8/2002 | Viola et al. |
| 6,450,173 B1 | 9/2002 | Forsell |
| 6,450,946 B1 | 9/2002 | Forsell |
| 6,453,907 B1 | 9/2002 | Forsell |
| 6,454,698 B1 | 9/2002 | Forsell |
| 6,454,699 B1 | 9/2002 | Forsell |
| 6,454,700 B1 | 9/2002 | Forsell |
| 6,454,701 B1 | 9/2002 | Forsell |
| 6,456,883 B1 | 9/2002 | Torgerson et al. |
| 6,460,543 B1 | 10/2002 | Forsell |
| 6,461,292 B1 | 10/2002 | Forsell |
| 6,461,293 B1 | 10/2002 | Forsell |
| 6,463,935 B1 | 10/2002 | Forsell |
| 6,464,628 B1 | 10/2002 | Forsell |
| 6,464,653 B1 | 10/2002 | Hovland et al. |
| 6,464,655 B1 | 10/2002 | Shahinpoor |
| 6,470,892 B1 | 10/2002 | Forsell |
| 6,471,635 B1 | 10/2002 | Forsell |
| 6,471,688 B1 | 10/2002 | Harper et al. |
| 6,475,136 B1 | 11/2002 | Forsell |
| 6,480,946 B1 | 11/2002 | Tomishima |
| 6,482,145 B1 | 11/2002 | Forsell |
| 6,502,161 B1 | 12/2002 | Perego et al. |
| 6,503,189 B1 | 1/2003 | Forsell |
| 6,516,282 B2 | 2/2003 | Hedlund |
| 6,571,127 B1 | 5/2003 | Ben-Haim et al. |
| 6,572,585 B2 | 6/2003 | Choi |
| 6,576,010 B2 | 6/2003 | Ulert et al. |
| 6,589,229 B1 | 7/2003 | Connelly et al. |
| 6,600,953 B2 | 7/2003 | Flesler et al. |
| 6,638,208 B1 | 10/2003 | Natarajan et al. |
| 6,638,303 B1 | 10/2003 | Campbell |
| 6,640,309 B2 | 10/2003 | Doblar |
| 6,650,943 B1 | 11/2003 | Whitehurst et al. |
| 6,659,936 B1 | 12/2003 | Furness et al. |
| 6,678,561 B2 | 1/2004 | Forsell |
| 6,689,085 B1 | 2/2004 | Rubenstein et al. |
| 6,709,385 B2 | 3/2004 | Forsell |
| 6,740,075 B2 | 5/2004 | Lebel et al. |
| 6,772,011 B2 | 8/2004 | Dolgin |
| 6,839,393 B1 | 1/2005 | Sidiropoulos |
| 6,862,479 B1 | 3/2005 | Whitehurst et al. |
| 6,895,280 B2 | 5/2005 | Meadows et al. |
| 6,896,651 B2 | 5/2005 | Gross et al. |
| 6,911,002 B2 | 6/2005 | Fierro |
| 6,928,338 B1 | 8/2005 | Buchser et al. |
| 6,929,625 B2 | 8/2005 | Bierman |
| 6,948,918 B2 | 9/2005 | Hansen |
| 6,953,429 B2 | 10/2005 | Forsell |
| 6,954,871 B2 | 10/2005 | Kuhn |
| 6,960,233 B1 | 11/2005 | Berg et al. |
| 6,979,351 B2 | 12/2005 | Forsell et al. |
| 6,988,983 B2 | 1/2006 | Connors et al. |
| 7,003,684 B2 | 2/2006 | Chang |
| 7,011,624 B2 | 3/2006 | Forsell |
| 7,017,583 B2 | 3/2006 | Forsell |
| 7,043,295 B2 | 5/2006 | Starkebaum |
| 7,066,922 B2 | 6/2006 | Angel et al. |
| 7,108,686 B2 | 9/2006 | Burke et al. |
| 7,165,153 B2 | 1/2007 | Vogt |
| 7,207,936 B2 | 4/2007 | Forsell |
| 7,214,233 B2 | 5/2007 | Gannoe et al. |
| 7,217,236 B2 | 5/2007 | Calderon et al. |
| 7,222,224 B2 | 5/2007 | Woo |
| 7,235,044 B2 | 6/2007 | Forsell |
| 7,238,165 B2 | 7/2007 | Vincent |
| 7,250,037 B2 | 7/2007 | Shermer et al. |
| 7,311,690 B2 | 12/2007 | Burnett |
| 7,313,639 B2 | 12/2007 | Perego et al. |
| 7,330,753 B2 | 2/2008 | Policker et al. |
| 7,338,437 B2 | 3/2008 | Forsell |
| 7,367,938 B2 | 5/2008 | Forsell |
| 7,371,208 B2 | 5/2008 | Forsell |
| 7,395,822 B1 | 7/2008 | Burton et al. |
| 7,407,479 B2 | 8/2008 | Forsell |
| 7,407,481 B2 | 8/2008 | Forsell |
| 7,442,165 B2 | 10/2008 | Forsell |
| 7,455,663 B2 | 11/2008 | Bikovsky |
| 7,569,050 B2 | 8/2009 | Moberg et al. |
| 7,621,863 B2 | 11/2009 | Forsell |
| 7,648,455 B2 | 1/2010 | Forsell |
| 7,666,132 B2 | 2/2010 | Forsell |
| 7,669,601 B2 | 3/2010 | Tal |
| 7,844,342 B2 | 11/2010 | Dlugos et al. |
| 7,846,160 B2 | 12/2010 | Payne et al. |
| 7,931,582 B2 | 4/2011 | Forsell |
| 7,972,354 B2 | 7/2011 | Prestezog et al. |
| 7,987,853 B2 | 8/2011 | Swann et al. |
| 7,988,616 B2 | 8/2011 | Forsell |
| 7,991,476 B2 | 8/2011 | Nachum |
| 8,070,768 B2 | 12/2011 | Kim et al. |
| 8,096,938 B2 | 1/2012 | Forsell |
| 8,096,939 B2 | 1/2012 | Forsell |
| 8,126,558 B2 | 2/2012 | Forsell |
| 8,195,296 B2 | 6/2012 | Longhini et al. |
| 8,287,444 B2 | 10/2012 | Forsell |
| 8,290,594 B2 | 10/2012 | Forsell |
| 8,313,423 B2 | 11/2012 | Forsell |
| 8,795,153 B2 | 8/2014 | Forsell |
| 2001/0011543 A1 | 8/2001 | Forsell |
| 2001/0016738 A1 | 8/2001 | Harrington et al. |
| 2001/0041824 A1 | 11/2001 | Zappala |
| 2002/0022759 A1 | 2/2002 | Forsell |
| 2002/0028846 A1 | 3/2002 | Yeager et al. |
| 2002/0028980 A1 | 3/2002 | Thierfelder et al. |
| 2002/0032462 A1 | 3/2002 | Houser et al. |
| 2002/0040208 A1 | 4/2002 | Flaherty et al. |
| 2002/0055711 A1 | 5/2002 | Lavi et al. |
| 2002/0072698 A1 | 6/2002 | Chiang et al. |
| 2002/0072759 A1 | 6/2002 | Fry |
| 2002/0095139 A1 | 7/2002 | Keogh et al. |
| 2002/0095164 A1 | 7/2002 | Andreas et al. |
| 2002/0111577 A1 | 8/2002 | Sirimanne et al. |
| 2002/0120219 A1 | 8/2002 | Hovland et al. |

(56) References Cited

U.S. PATENT DOCUMENTS

| | | |
|---|---|---|
| 2002/0151922 A1 | 10/2002 | Hogendijk et al. |
| 2002/0165575 A1 | 11/2002 | Saleh |
| 2002/0183588 A1 | 12/2002 | Fierro |
| 2003/0009201 A1 | 1/2003 | Forsell |
| 2003/0009221 A1 | 1/2003 | Forsell |
| 2003/0014010 A1 | 1/2003 | Carpenter et al. |
| 2003/0014086 A1 | 1/2003 | Sharma |
| 2003/0021822 A1 | 1/2003 | Lloyd |
| 2003/0032855 A1 | 2/2003 | Shahinpoor |
| 2003/0032857 A1 | 2/2003 | Forsell |
| 2003/0040804 A1 | 2/2003 | Stack et al. |
| 2003/0050591 A1 | 3/2003 | Patrick McHale |
| 2003/0055442 A1 | 3/2003 | Laufer et al. |
| 2003/0060814 A1 | 3/2003 | Capuano et al. |
| 2003/0060893 A1 | 3/2003 | Forsell |
| 2003/0066536 A1 | 4/2003 | Forsell |
| 2003/0069547 A1 | 4/2003 | Gonon |
| 2003/0088148 A1 | 5/2003 | Forsell |
| 2003/0092962 A1 | 5/2003 | Forsell |
| 2003/0100929 A1 | 5/2003 | Forsell |
| 2003/0105385 A1 | 6/2003 | Forsell |
| 2003/0109771 A1 | 6/2003 | Forsell |
| 2003/0114729 A1 | 6/2003 | Forsell |
| 2003/0125605 A1 | 7/2003 | Forsell |
| 2003/0125768 A1 | 7/2003 | Peter |
| 2003/0144575 A1 | 7/2003 | Forsell |
| 2003/0144648 A1 | 7/2003 | Forsell |
| 2003/0163029 A1 | 8/2003 | Sonnenschein et al. |
| 2003/0200407 A1 | 10/2003 | Osaka |
| 2003/0208247 A1 | 11/2003 | Spinelli et al. |
| 2003/0220621 A1 | 11/2003 | Arkinstall |
| 2003/0231543 A1 | 12/2003 | Matsui |
| 2003/0233143 A1 | 12/2003 | Gharib et al. |
| 2004/0006291 A1 | 1/2004 | Rehrig |
| 2004/0015041 A1 | 1/2004 | Melvin |
| 2004/0024285 A1 | 2/2004 | Muckter |
| 2004/0024419 A1 | 2/2004 | Slepian et al. |
| 2004/0034275 A1 | 2/2004 | Forsell |
| 2004/0068299 A1 | 4/2004 | Laske et al. |
| 2004/0089313 A1 | 5/2004 | Utley et al. |
| 2004/0098113 A1 | 5/2004 | Forsell et al. |
| 2004/0098545 A1 | 5/2004 | Pline et al. |
| 2004/0102804 A1 | 5/2004 | Chin |
| 2004/0122526 A1 | 6/2004 | Imran |
| 2004/0122527 A1 | 6/2004 | Imran |
| 2004/0147871 A1 | 7/2004 | Burnett |
| 2004/0162568 A1 | 8/2004 | Saadat et al. |
| 2004/0172141 A1 | 9/2004 | Stack et al. |
| 2004/0177918 A1 | 9/2004 | Murata et al. |
| 2004/0186344 A1 | 9/2004 | Jannuzzi |
| 2004/0215159 A1 | 10/2004 | Forsell |
| 2004/0215283 A1 | 10/2004 | Camps et al. |
| 2004/0220516 A1 | 11/2004 | Solomon et al. |
| 2004/0230718 A1 | 11/2004 | Polzin et al. |
| 2004/0236877 A1 | 11/2004 | Burton |
| 2004/0242956 A1 | 12/2004 | Scorvo |
| 2004/0249451 A1 | 12/2004 | Lu et al. |
| 2004/0260316 A1 | 12/2004 | Knudson et al. |
| 2005/0009178 A1 | 1/2005 | Yost et al. |
| 2005/0038484 A1 | 2/2005 | Knudson et al. |
| 2005/0055025 A1 | 3/2005 | Zacouto et al. |
| 2005/0060030 A1 | 3/2005 | Lashinski et al. |
| 2005/0075697 A1 | 4/2005 | Olson et al. |
| 2005/0192642 A1 | 9/2005 | Forsell |
| 2005/0209633 A1 | 9/2005 | Callister et al. |
| 2005/0209652 A1 | 9/2005 | Whitehurst et al. |
| 2005/0222678 A1 | 10/2005 | Lashinski et al. |
| 2005/0238506 A1 | 10/2005 | Mescher et al. |
| 2005/0240229 A1 | 10/2005 | Whitehurst et al. |
| 2005/0245957 A1 | 11/2005 | Starkebaum et al. |
| 2005/0256587 A1 | 11/2005 | Egan |
| 2005/0261712 A1 | 11/2005 | Balbierz et al. |
| 2005/0266042 A1 | 12/2005 | Tseng |
| 2005/0267405 A1 | 12/2005 | Shah |
| 2005/0267596 A1 | 12/2005 | Chen et al. |
| 2005/0276261 A1 | 12/2005 | Kim |
| 2006/0025855 A1 | 2/2006 | Lashinski et al. |
| 2006/0030887 A1 | 2/2006 | Letort et al. |
| 2006/0034358 A1 | 2/2006 | Okamura |
| 2006/0047180 A1 | 3/2006 | Hegde et al. |
| 2006/0069414 A1 | 3/2006 | Imran et al. |
| 2006/0083899 A1 | 4/2006 | Burazin et al. |
| 2006/0127246 A1 | 6/2006 | Forsell |
| 2006/0129028 A1 | 6/2006 | Krakousky |
| 2006/0142635 A1 | 6/2006 | Forsell |
| 2006/0149124 A1 | 7/2006 | Forsell |
| 2006/0149129 A1 | 7/2006 | Watts et al. |
| 2006/0161217 A1 | 7/2006 | Jaax et al. |
| 2006/0167539 A1 | 7/2006 | Mcewan |
| 2006/0173238 A1 | 8/2006 | Starkebaum |
| 2006/0195139 A1 | 8/2006 | Gertner |
| 2006/0200194 A1 | 9/2006 | Yun |
| 2006/0212055 A1 | 9/2006 | Karabey et al. |
| 2006/0224177 A1 | 10/2006 | Finitsis |
| 2006/0229688 A1 | 10/2006 | McClure et al. |
| 2006/0235482 A1 | 10/2006 | Forsell |
| 2006/0247719 A1 | 11/2006 | Maschino et al. |
| 2006/0247721 A1 | 11/2006 | Maschino et al. |
| 2006/0247722 A1 | 11/2006 | Maschino et al. |
| 2006/0257446 A1 | 11/2006 | Tropsha et al. |
| 2007/0015959 A1 | 1/2007 | Forsell |
| 2007/0038232 A1 | 2/2007 | Kraemer |
| 2007/0038831 A1 | 2/2007 | Kim |
| 2007/0049790 A1 | 3/2007 | Wagner et al. |
| 2007/0073099 A1 | 3/2007 | Forsell |
| 2007/0092862 A1 | 4/2007 | Gerber |
| 2007/0109019 A1 | 5/2007 | Wu |
| 2007/0121389 A1 | 5/2007 | Wu |
| 2007/0156204 A1 | 7/2007 | Denker et al. |
| 2007/0162670 A1 | 7/2007 | Yang |
| 2007/0167670 A1 | 7/2007 | Coleman et al. |
| 2007/0193632 A1 | 8/2007 | Shu |
| 2007/0204924 A1 | 9/2007 | Delgiacco et al. |
| 2007/0232848 A1 | 10/2007 | Forsell |
| 2007/0250020 A1 | 10/2007 | Kim et al. |
| 2007/0255335 A1 | 11/2007 | Herbert et al. |
| 2007/0255336 A1 | 11/2007 | Herbert et al. |
| 2007/0265675 A1 | 11/2007 | Lund et al. |
| 2008/0004487 A1 | 1/2008 | Haverfield |
| 2008/0045783 A1 | 2/2008 | Forsell |
| 2008/0051718 A1 | 2/2008 | Kavazov et al. |
| 2008/0065167 A1 | 3/2008 | Boggs et al. |
| 2008/0086179 A1 | 4/2008 | Sharma |
| 2008/0103544 A1 | 5/2008 | Weiner |
| 2008/0139873 A1 | 6/2008 | Peters et al. |
| 2008/0139980 A1 | 6/2008 | Fladl et al. |
| 2008/0154256 A1 | 6/2008 | Payne et al. |
| 2008/0178889 A1 | 7/2008 | Tal |
| 2008/0195228 A1 | 8/2008 | Uno et al. |
| 2008/0200753 A1 | 8/2008 | Forsell |
| 2008/0214888 A1 | 9/2008 | Shalom |
| 2008/0245371 A1 | 10/2008 | Gruber |
| 2008/0269548 A1 | 10/2008 | Vecchiotti et al. |
| 2008/0275296 A1 | 11/2008 | Forsell |
| 2009/0018388 A1 | 1/2009 | Forsell |
| 2009/0024108 A1 | 1/2009 | Lee-Sepsick et al. |
| 2009/0054725 A1 | 2/2009 | Forsell |
| 2009/0082705 A1 | 3/2009 | Asfora |
| 2009/0131959 A1 | 5/2009 | Rolland |
| 2009/0216076 A1 | 8/2009 | Kain |
| 2009/0240100 A1 | 9/2009 | Forsell |
| 2009/0240294 A1 | 9/2009 | Forsell |
| 2009/0247817 A1 | 10/2009 | Forsell |
| 2009/0247818 A1 | 10/2009 | Forsell |
| 2009/0248033 A1 | 10/2009 | Forsell |
| 2009/0248109 A1 | 10/2009 | Forsell |
| 2009/0250068 A1 | 10/2009 | Forsell |
| 2009/0254106 A1 | 10/2009 | Forsell |
| 2009/0266366 A1 | 10/2009 | Swann et al. |
| 2010/0016657 A1 | 1/2010 | Robertson et al. |
| 2010/0145138 A1 | 6/2010 | Forsell |
| 2010/0145139 A1 | 6/2010 | Forsell |
| 2010/0217067 A1 | 8/2010 | Forsell |
| 2010/0217289 A1 | 8/2010 | Forsell |

(56) References Cited

U.S. PATENT DOCUMENTS

| | | |
|---|---|---|
| 2010/0222894 A1 | 9/2010 | Forsell |
| 2010/0286735 A1 | 11/2010 | Garfield et al. |
| 2010/0305656 A1 | 12/2010 | Imran et al. |
| 2010/0312047 A1 | 12/2010 | Forsell |
| 2010/0312048 A1 | 12/2010 | Forsell |
| 2010/0312049 A1 | 12/2010 | Forsell |
| 2010/0312050 A1 | 12/2010 | Forsell |
| 2010/0312163 A1 | 12/2010 | Forsell |
| 2010/0312164 A1 | 12/2010 | Forsell |
| 2010/0312356 A1 | 12/2010 | Forsell |
| 2010/0318116 A1 | 12/2010 | Forsell |
| 2010/0318117 A1 | 12/2010 | Forsell |
| 2010/0318118 A1 | 12/2010 | Forsell |
| 2010/0324360 A1 | 12/2010 | Forsell |
| 2010/0324361 A1 | 12/2010 | Forsell |
| 2010/0324362 A1 | 12/2010 | Forsell |
| 2010/0324591 A1 | 12/2010 | Forsell |
| 2010/0331614 A1 | 12/2010 | Forsell |
| 2010/0331615 A1 | 12/2010 | Forsell |
| 2010/0331616 A1 | 12/2010 | Forsell |
| 2010/0331617 A1 | 12/2010 | Forsell |
| 2010/0331945 A1 | 12/2010 | Forsell |
| 2010/0332000 A1 | 12/2010 | Forsell |
| 2011/0009894 A1 | 1/2011 | Forsell |
| 2011/0009896 A1 | 1/2011 | Forsell |
| 2011/0009897 A1 | 1/2011 | Forsell |
| 2011/0015473 A1 | 1/2011 | Forsell |
| 2011/0015474 A1 | 1/2011 | Forsell |
| 2011/0040143 A1 | 2/2011 | Forsell |
| 2011/0066254 A1 | 3/2011 | Forsell |
| 2011/0087337 A1 | 4/2011 | Forsell |
| 2011/0144468 A1* | 6/2011 | Boggs et al. ................. 600/373 |
| 2011/0172693 A1 | 7/2011 | Forsell |
| 2011/0184230 A1 | 7/2011 | Forsell |
| 2011/0192402 A1 | 8/2011 | Forsell |
| 2011/0196192 A1 | 8/2011 | Forsell |
| 2011/0196193 A1 | 8/2011 | Forsell |
| 2011/0196194 A1 | 8/2011 | Forsell |
| 2011/0196271 A1 | 8/2011 | Forsell |
| 2011/0196371 A1 | 8/2011 | Forsell |
| 2011/0196391 A1 | 8/2011 | Forsell |
| 2011/0196411 A1 | 8/2011 | Forsell |
| 2011/0196435 A1 | 8/2011 | Forsell |
| 2011/0196466 A1 | 8/2011 | Forsell |
| 2011/0196476 A1 | 8/2011 | Forsell |
| 2011/0196481 A1 | 8/2011 | Forsell |
| 2011/0196482 A1 | 8/2011 | Forsell |
| 2011/0196483 A1 | 8/2011 | Forsell |
| 2011/0196484 A1 | 8/2011 | Forsell |
| 2011/0196485 A1 | 8/2011 | Forsell |
| 2011/0196486 A1 | 8/2011 | Forsell |
| 2011/0196505 A1 | 8/2011 | Forsell |
| 2011/0196506 A1 | 8/2011 | Forsell |
| 2011/0201870 A1 | 8/2011 | Forsell |
| 2011/0201871 A1 | 8/2011 | Forsell |
| 2011/0201873 A1 | 8/2011 | Forsell |
| 2011/0202041 A1 | 8/2011 | Forsell |
| 2011/0202129 A1 | 8/2011 | Fofsell |
| 2011/0202131 A1 | 8/2011 | Forsell |
| 2011/0208231 A1 | 8/2011 | Forsell |
| 2011/0218394 A1 | 9/2011 | Forsell |
| 2011/0224787 A1 | 9/2011 | Forsell |
| 2011/0230930 A1 | 9/2011 | Forsell |
| 2011/0263928 A1 | 10/2011 | Forsell |
| 2011/0288499 A1 | 11/2011 | Forsell |
| 2012/0029550 A1 | 2/2012 | Forsell |

FOREIGN PATENT DOCUMENTS

| | | |
|---|---|---|
| DE | 15 41 262 | 6/1969 |
| DE | 19511998 | 10/1996 |
| DE | 199 09 427 | 5/2000 |
| DE | 101 04 806 | 8/2002 |
| EP | 0102548 | 3/1984 |
| EP | 01 343 40 | 3/1985 |
| EP | 0 200 286 | 11/1986 |
| EP | 0 252 258 | 1/1988 |
| EP | 0300552 | 1/1989 |
| EP | 0 348 114 | 12/1989 |
| EP | 0 372 311 | 6/1990 |
| EP | 0378251 | 7/1990 |
| EP | 0 393 714 | 10/1990 |
| EP | 0412191 | 2/1991 |
| EP | 0 532 162 | 3/1993 |
| EP | 0 583 012 | 2/1994 |
| EP | 0611561 | 9/1994 |
| EP | 0626154 | 11/1994 |
| EP | 0876808 | 11/1998 |
| EP | 1 004 330 | 5/2000 |
| EP | 1 033 142 | 9/2000 |
| EP | 1 072 238 | 1/2001 |
| EP | 1 275 344 | 1/2003 |
| EP | 1 514 526 | 3/2005 |
| EP | 1563814 | 8/2005 |
| EP | 1563866 | 8/2005 |
| EP | 1563886 | 8/2005 |
| EP | 1 586 283 | 10/2005 |
| EP | 1 600 183 | 11/2005 |
| EP | 1598030 | 11/2005 |
| EP | 1 602 334 | 12/2005 |
| EP | 1 681 041 | 7/2006 |
| EP | 1 878 452 | 1/2008 |
| EP | 1 884 259 A1 | 2/2008 |
| EP | 1 913 880 | 4/2008 |
| FR | 2 248 015 | 5/1975 |
| FR | 2621248 A1 | 7/1989 |
| FR | 2688693 | 9/1993 |
| FR | 2692777 | 12/1993 |
| FR | 27565485 | 6/1998 |
| FR | 2797181 | 2/2001 |
| FR | 2908979 | 5/2008 |
| GB | 8 856 74 | 12/1961 |
| GB | 1174814 | 12/1969 |
| GB | 1194358 | 6/1970 |
| GB | 2021956 | 12/1979 |
| JP | 58-190437 | 11/1983 |
| JP | 62-8752 | 1/1987 |
| JP | 63-18177 | 7/1988 |
| JP | 1-305945 | 12/1989 |
| JP | 2-211170 | 8/1990 |
| JP | 3-63047 | 3/1991 |
| JP | 3-158154 | 7/1991 |
| JP | 2002-517277 | 6/2002 |
| SU | 906-526 | 2/1982 |
| SU | 1 635 980 | 3/1991 |
| WO | WO 84/01282 | 4/1984 |
| WO | WO 91/00094 | 1/1991 |
| WO | WO 94/27504 | 12/1994 |
| WO | WO 96/01597 | 1/1996 |
| WO | WO 96/11036 | 4/1996 |
| WO | WO 96/39932 | 12/1996 |
| WO | WO 97/03616 | 2/1997 |
| WO | WO 97/41799 | 11/1997 |
| WO | WO 98/06358 | 2/1998 |
| WO | WO 98/50099 | 11/1998 |
| WO | WO 99/18885 | 4/1999 |
| WO | WO 99/63907 | 12/1999 |
| WO | WO 00/09047 | 2/2000 |
| WO | WO 00/09048 | 2/2000 |
| WO | WO 00/15158 | 3/2000 |
| WO | WO 00/16686 | 3/2000 |
| WO | WO 00/21606 | 4/2000 |
| WO | WO 00/33825 | 6/2000 |
| WO | WO 01/12075 | 2/2001 |
| WO | WO 01/12078 | 2/2001 |
| WO | WO 01/12108 | 2/2001 |
| WO | WO 01/45486 | 6/2001 |
| WO | WO 01/45487 | 6/2001 |
| WO | WO 01/45590 | 6/2001 |
| WO | WO 01/47431 | 7/2001 |
| WO | WO 01/47435 | 7/2001 |
| WO | WO 01/47439 | 7/2001 |
| WO | WO 01/47575 | 7/2001 |

(56) References Cited

FOREIGN PATENT DOCUMENTS

| | | |
|---|---|---|
| WO | WO 01/50832 | 7/2001 |
| WO | WO 0147434 | 7/2001 |
| WO | WO 01/54615 | 8/2001 |
| WO | WO 01/58391 | 8/2001 |
| WO | WO 01/67964 | 9/2001 |
| WO | WO 02/38217 | 5/2002 |
| WO | WO 02/39959 | 5/2002 |
| WO | WO 02/40083 | 5/2002 |
| WO | WO 02/053210 | 7/2002 |
| WO | WO 02/058563 | 8/2002 |
| WO | WO 02/087657 | 11/2002 |
| WO | WO 02/100481 | 12/2002 |
| WO | WO 03/002192 | 1/2003 |
| WO | WO 03/033054 | 4/2003 |
| WO | WO 03/086507 | 10/2003 |
| WO | WO 2004/012806 | 2/2004 |
| WO | WO 2004/018037 | 3/2004 |
| WO | WO 2004/019765 | 3/2004 |
| WO | WO 2004/060171 | 7/2004 |
| WO | WO 2004/071684 | 8/2004 |
| WO | WO 2004/087233 | 10/2004 |
| WO | WO 2004/101029 | 11/2004 |
| WO | WO 2005/072169 | 8/2005 |
| WO | WO 2005/084730 | 9/2005 |
| WO | WO 2005/105003 | 11/2005 |
| WO | WO 2006/014496 | 2/2006 |
| WO | WO 2006/044194 | 4/2006 |
| WO | WO 2006/114004 | 11/2006 |
| WO | WO 2006/122285 | 11/2006 |
| WO | WO 2006/134106 | 12/2006 |
| WO | WO 2007/017880 | 2/2007 |
| WO | WO 2007/041795 | 4/2007 |
| WO | WO 2007/051563 | 5/2007 |
| WO | WO 2007/106303 | 9/2007 |
| WO | WO 2007/109759 | 9/2007 |
| WO | WO 2007/121525 | 11/2007 |
| WO | WO 2007/124128 | 11/2007 |
| WO | WO 2007/137026 | 11/2007 |
| WO | WO 2007/149555 | 12/2007 |
| WO | WO 2008/100390 | 8/2008 |
| WO | WO 2008/135988 | 11/2008 |
| WO | WO 2009/010799 | 1/2009 |
| WO | WO 2009/048382 | 4/2009 |
| WO | WO 2009/048389 | 4/2009 |
| WO | WO 2009/096854 | 8/2009 |
| WO | WO 2009/096865 | 8/2009 |
| WO | WO 2009/096868 | 8/2009 |
| WO | WO 2009/115645 | 9/2009 |

OTHER PUBLICATIONS

U.S. Appl. No. 11/988,450, filed May 27, 2009, Forsell.
Extended European Search Report in EP patent application 09819499.6 dated Nov. 29, 2012.
"NPC-102 N Medical Angioplasty Sensor" web page at www.novasensor.com/catalog/NPC_102.html and NPC-102 Datasheet, circa 1997, retrieved from the Internet Archives for www.novasensor.com.
Webster's II New River side University, 1984, pp. 573,1000.
Anand, Sneh. "Electrical Pacing of the Ampullary Isthmic Junction for Contraception", IEEE Engineering in Medicine & Biology $10^{th}$ Annual International Conference, 1988.
S. K. Guha et al., "Feasibility study of the reversible occlusion device for the vas deferens," Medical and Biological Engineering and Computing, vol. 14, No. 1, Jan. 1976, pp. 15-18.
Enclyclopedia Britannica definition of "ductus deferens" (retrieved from the Internet May 22, 2013: URL: http://www.britannica.com/EBchecked/topic/173003/ductus-deferens?sections=173003main &view=print).
U.S. Appl. No. 12/285,792 (Forsell) filed Oct. 14, 2008.
U.S. Appl. No. 12/758,684 (Forsell) filed Apr. 12, 2010.
U.S. Appl. No. 12/758,694 (Forsell) filed Apr. 12, 2010.
U.S. Appl. No. 13/122,907 (Forsell) filed Apr. 6, 2011.
U.S. Appl. No. 13/123,145 (Forsell) filed Apr. 8, 2011.
U.S. Appl. No. 13/123,425 (Forsell) filed Apr. 8, 2011.
International Search Report for PCT/SE2009/051127.
Written Opinion of the International Searching Authority for PCT/SE2009/051127.

* cited by examiner

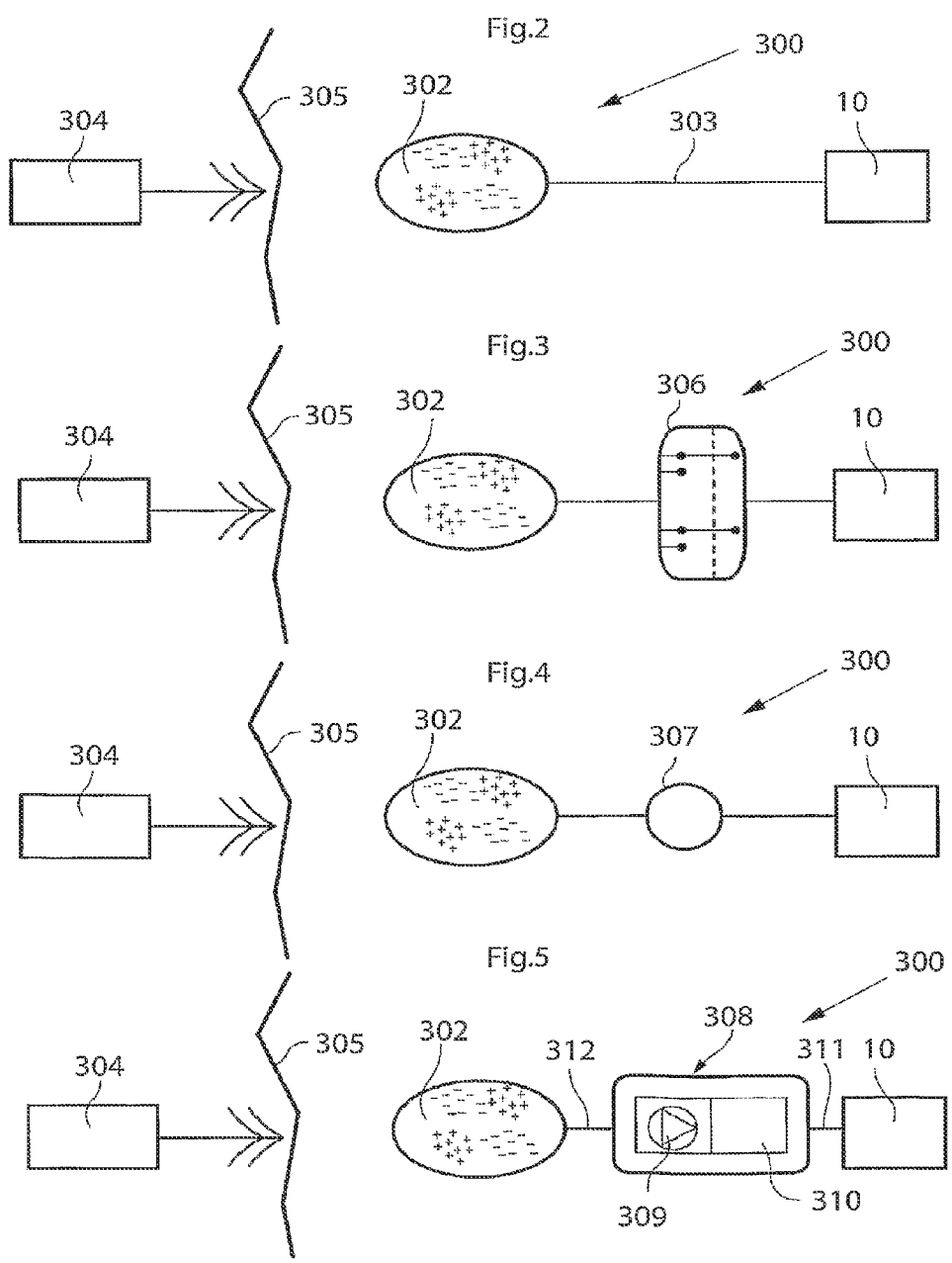

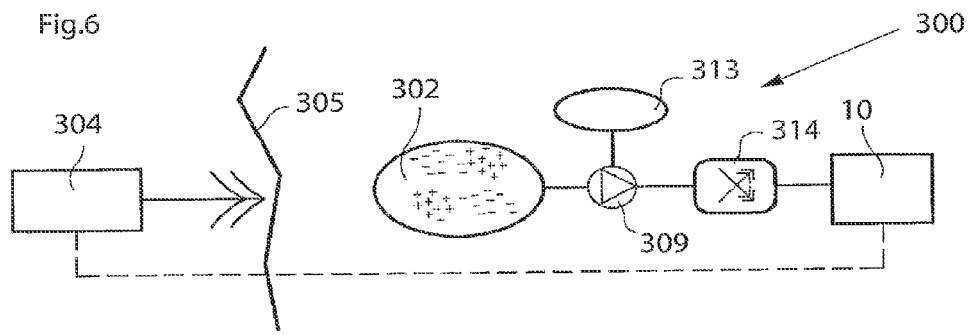
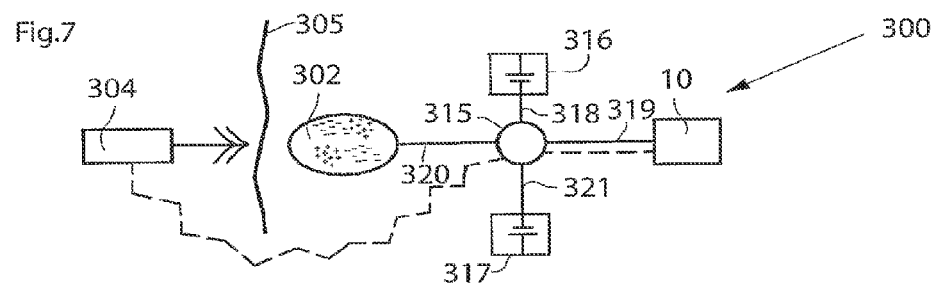
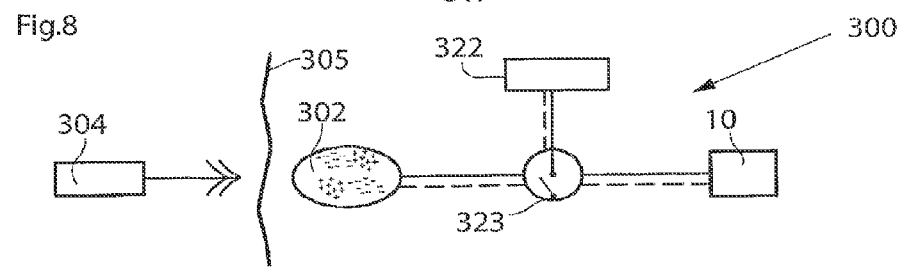
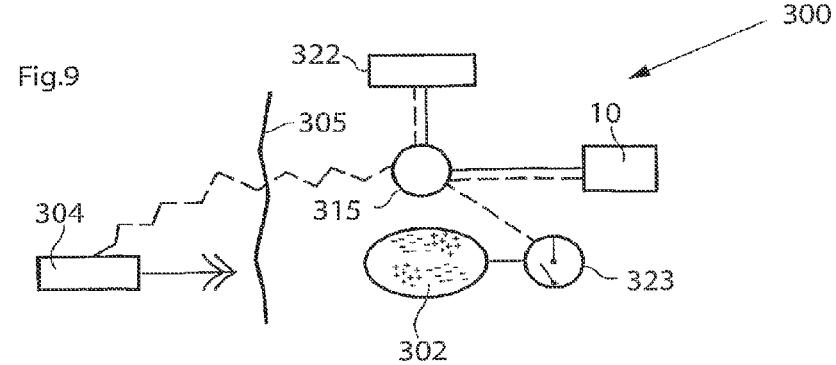

SYSTEM, AN APPARATUS, AND A METHOD FOR TREATING A SEXUAL DYSFUNCTIONAL FEMALE PATIENT

This application is a Continuation of U.S. patent application Ser. No. 13/123,145 filed Apr. 7, 2011 now granted U.S. Pat. No. 8,874,215 and a National Stage Briny of PCT/SE2009/051127 filed Oct. 9, 2009.

TECHNICAL FIELD

The present invention relates to the treatment of sexual dysfunction in a female patient, as well as a system and an apparatus for the purpose.

BACKGROUND

A lot of attention has been given to male sexual disorders including impotency. This has lead to the availability of a number of treatment options for males, including pharmaceuticals such as Viagra.

In contrast, there is a lack of therapies for treating Female sexual dysfunction. Female sexual dysfunction such as disorders of sexual desire, arousal or orgasm is a common problem, affecting up to 43% of all women (Pauls et al, Obstret Gynecol Surv, 2005 60(3):3196-205). Both biological and psychological factors contribute to FSD.

Available treatments include psychological counselling to pairs or individuals. Where side effects of medication contribute to FSD, altering medication or dosage may help.

During sexual arousal of the female, vasocongestion of the pelvic region leads to engorgement of the genitalia with blood leading to swelling of the external genitalia and erection of the clitoris. This is accompanied by lubrication of the vagina. In the female, the corpus cavernosa are two paired symmetrical extensions of the clitoris and engorgement of these is an important step during sexual arousal of the female.

Female sexual arousal is enhanced by stimulation of the vulva, by touching or caressing the clitoris, which contributes to arousal.

Hand held or other external devices that stimulate the clitoris are well-known. For example U.S. Pat. No. 7,081,087 discloses a sexual aid that vibrates. There has been proposed a device for treating FSD that applies a vacuum or suction to the clitoris. This will create a negative pressure that promotes the engorgement of the clitoris with blood (Hovland Claire, U.S. Pat. No. 6,464,653).

The proposed device is implanted. An advantage with the implantation of a stimulating device is that it is always at hand and can conveniently be switched on before sexual intercourse. Hand held devices are more likely to cause embarrassment.

The local administration of prostaglandins to the female genetalia in order to treat FSD has been described in U.S. Pat. No. 6,486,207).

The implantation of an electrode that stimulates the peripheral nerves of the vulva has been described (US 2008/0103544).

In spite of the available treatments there is still a need for improved treatment of female sexual dysfunction.

SUMMARY OF THE INVENTION

It is an object of the present invention to obviate at least some of the disadvantages in the prior art.

One advantage of the present invention is that the likelihood to get orgasm will increase by the stimulation device.

Another advantage of the present invention is that the sexual response to sexual stimuli will increase.

In a first aspect there is provided an apparatus for treating a sexual dysfunctional female patient, comprising a stimulation device adapted to stimulate an erectile blood flow passageway to increase the amount of blood in the female erectile tissue and thereby obtaining engorgement with blood of the female erectile tissue by affecting said erectile blood flow passageway.

In a second aspect there is provided a system comprising an apparatus according to the invention.

In a third aspect there is provided an operation method using an apparatus according to the invention, comprising the steps of: a) creating an opening in the skin or vaginal wall of the female patient b) dissecting at least one area of the female erectile tissue, and c) placing the stimulation device within said area, adapted to postoperatively stimulate said female erectile tissue on patient command.

Further aspects and embodiments are defined in the appended claims, which are specifically incorporated herein by reference.

Definitions

The term "female erectile tissue" refers to tissue of the female sexual organs that before or during sexual intercourse are filled with blood including the corpora cavernosa, the vestibular bulbs and the clitoris The term "free flow" as used throughout the description and the terms denotes a fluid passageway unaffected by any artificial stimulation in any direction, such as valves or return valves.

The term "tissue" as used throughout the description and the claims denotes a cellular organizational level intermediate between cells and a complete organism. Hence, a tissue is an ensemble of cells, not necessarily identical, but from the same origin, that together carry out a specific function. For example tissue includes bone.

In general terms the present invention relates an apparatus and methods of treating a sexual dysfunctional female patient which comprises a stimulation device for stimulating the erectile tissues of a female patient. In accordance with the invention stimulation can be performed by stimulating so as to affect blood passageways to or from the erectile tissues. The present invention also relates to the accomplishment of stimulation directly on the corpus cavernosa and thereby affects stimulation of glands assisting with their secretion of fluids associated with natural engorgement. These mentioned routes of stimulation can either be performed separately or in combination with any apparatus of the invention.

In a first aspect there is provided an apparatus for treating a sexual dysfunctional female patient, comprising a stimulation device adapted to stimulate an erectile blood flow passageway to increase the amount of blood in the female erectile tissue and thereby obtaining engorgement with blood of the female erectile tissue by affecting said erectile blood flow passageway.

In one embodiment there is provided an apparatus comprising a stimulation device that is able to restrict the blood flow passageway leaving the female erectile tissue.

In one embodiment there is provided an apparatus, wherein said stimulation device engages at least one selected from the group consisting of: a venous blood vessel leading from said female erectile tissue, a corpus cavernosum, a vestibular bulb and a muscle affecting blood flow that drains the female erectile tissue; said stimulation device being adapted to temporarily and at least partially restrict the cross-sectional area of such erectile blood flow passageway that drains the female erectile tissue.

In one embodiment there is provided an apparatus, comprising two or more stimulation devices post-operatively and non-invasively adjustable.

In one embodiment there is provided an apparatus, further comprising an implantable control unit for adjusting the stimulation device to temporarily contract the female erectile tissue to restrict the blood flow leaving the female erectile tissue.

In one embodiment there is provided an apparatus, comprising a control device comprising an implanted control unit adapted to control and adjust electrical parameters of said stimulation device, wherein said control unit is programmable from outside the female patient's body.

In one embodiment there is provided an apparatus, wherein the stimulation device comprises at least one electrical electrode to stimulate the female erectile tissue to achieve engorgement of said female erectile tissue.

In one embodiment there is provided an apparatus, further comprising an alarm adapted to generate an alarm signal in response to the lapse of a predetermined time period during which the stimulation device has been operating.

In one embodiment there is provided an apparatus, wherein the stimulation device comprises at least one elongated stimulation member adapted to form the stimulation member into at least a substantially closed loop around a portion of the female erectile tissue, the loop defining a stimulation opening.

In one embodiment there is provided an apparatus, wherein the stimulation device comprises at least two stimulation device electrodes.

In one embodiment there is provided an apparatus, wherein the stimulation device adapted to increase the arterial blood flow reaching the female erectile tissue causing engorgement with blood of the female erectile tissue.

In one embodiment there is provided an apparatus, wherein the flow of blood is increased by enlarging the cross-sectional area of the blood flow passageway, comprising said at least one artery.

In one embodiment there is provided an apparatus, wherein said stimulation device, comprising a heating member causing engorgement with blood of the female erectile tissue.

In one embodiment there is provided an apparatus, wherein said stimulation device stimulates a muscle related to said blood flow reaching the female erectile tissue.

In one embodiment there is provided an apparatus, wherein said stimulation device is adapted to stimulate said muscle, to cause relaxation of said muscle to increase said arterial blood flow.

In one embodiment there is provided an apparatus, wherein said stimulation device is adapted to stimulate said muscle excessively to relax said muscle.

In one embodiment there is provided an apparatus, wherein said stimulation device stimulates a muscle related to said blood flow leaving the female erectile tissue.

In one embodiment there is provided an apparatus, wherein said stimulation device is adapted to stimulate said muscle in order to induce contraction of said muscle to restrict said erectile blood flow passageway.

In one embodiment there is provided an apparatus, wherein said stimulation device is powered.

In one embodiment there is provided an apparatus, comprising a control device, wherein the control device controls the stimulation device to shift over time the stimulation from one area of one wall portion of the erectile blood flow passageway to another.

In one embodiment there is provided an apparatus, wherein said control device controls the stimulation device to cyclically propagate the stimulation to areas along the wall in the same or opposite direction of the flow in the patient's erectile blood flow passageway.

In one embodiment there is provided an apparatus, wherein the control device controls the stimulation device to propagate the stimulation of the areas in accordance with a determined stimulation pattern.

In one embodiment there is provided an apparatus, comprising a control device, wherein the control device controls the stimulation device to vary the intensity of the stimulation of the erectile blood flow passageway.

In one embodiment there is provided an apparatus, wherein the control device controls the stimulation device to cyclically vary the intensity of the stimulation of said erectile blood flow passageway.

In one embodiment there is provided an apparatus, wherein the control device controls the stimulation device to intermittently and individually stimulate different areas of the erectile blood flow passageway with pulses.

In one embodiment there is provided an apparatus, wherein the control device controls the stimulation device to intermittently stimulate the areas with the pulses.

In one embodiment there is provided an apparatus, wherein said pulses form pulse trains.

In one embodiment there is provided an apparatus, wherein the control device controls the stimulation device to vary the amplitudes of the pulses of the pulse trains.

In one embodiment there is provided an apparatus, wherein the control device controls the stimulation device to vary the off time periods between the individual pulses of each pulse train.

In one embodiment there is provided an apparatus, wherein the control device controls the stimulation device to vary the width of each pulse of the pulse trains.

In one embodiment there is provided an apparatus, wherein the control device controls the stimulation device to vary the frequency of the pulses of the pulse trains.

In one embodiment there is provided an apparatus, wherein the control device controls the stimulation device to vary the off time periods between the pulse trains.

In one embodiment there is provided an apparatus, wherein the control device controls the stimulation device to vary the length of each pulse train.

In one embodiment there is provided an apparatus, wherein the control device controls the stimulation device to vary the frequency of the pulse trains.

In one embodiment there is provided an apparatus, wherein the control device controls the stimulation device to vary the number of pulses of each pulse train.

In one embodiment there is provided an apparatus, wherein the stimulation device intermittently and individually electrically stimulates different areas of said erectile blood flow passageway.

In one embodiment there is provided an apparatus, wherein said stimulation device comprises at least one electrical electrode for engaging at least one portion of the wall of the erectile blood flow passageway and stimulating at least one portion of the wall thereof with electric pulses.

In one embodiment there is provided an apparatus, wherein the stimulation device comprises a plurality of electrical elements.

In one embodiment there is provided an apparatus, wherein the electrical elements are placed in a fixed orientation relative to one another.

In one embodiment there is provided an apparatus, wherein the stimulation device comprises a structure holding the electrical elements in the fixed orientation.

In one embodiment there is provided an apparatus, wherein the electrical elements form an elongate pattern of electrical elements, and the structure is applicable on the patient's erectile blood flow passageway such that the elongate pattern of electrical elements extends along at least one portion of the wall of the erectile blood flow passageway in the direction of the flow in the patient's erectile blood flow passageway and the elements abut the respective areas of the wall portion.

In one embodiment there is provided an apparatus, wherein said structure is integrated in said stimulation.

In one embodiment there is provided an apparatus, wherein said structure is separate from said stimulation device.

In one embodiment there is provided an apparatus, wherein said control device controls said stimulation device to electrically energize said electrical elements.

In one embodiment there is provided an apparatus, wherein said control device controls said stimulation device to cyclically energize each element with electric pulses.

In one embodiment there is provided an apparatus, wherein said control device controls said stimulation device to energize said electrical elements, such that a number or groups of said electrical elements are energized at the same time.

In one embodiment there is provided an apparatus, wherein said control device controls said stimulation device to energize said electrical elements, such that said electrical elements are energized one at a time in sequence or groups of said electrical elements are sequentially energized, either randomly or in accordance with a predetermined pattern.

In one embodiment there is provided an apparatus, wherein said electrical elements form an elongate pattern of electrical elements, and said elements are applicable on the patient's wall such that said elongate pattern of electrical elements extends along the wall at least one portion of the wall of the erectile blood flow passageway in the direction of the flow in the patient's erectile blood flow passageway and the elements abut the respective areas of the wall portion.

In one embodiment there is provided an apparatus, wherein said control device controls said stimulation device to successively energize said electrical elements longitudinally along said elongate pattern of electrical elements.

In one embodiment there is provided an apparatus, wherein said control device controls said stimulation device to successively energize said electrical elements along said elongate pattern of electrical elements in a direction opposite to, or in the same direction as, that of the flow in the patient's erectile blood flow passageway, when said stimulation device is applied on the patient's erectile blood flow passageway.

In one embodiment there is provided an apparatus, wherein said control device controls said stimulation device to successively energize said electrical elements from a position substantially at the center of the constricted wall portion towards both ends of the elongate pattern of electrical elements, when said stimulation device is applied on the erectile blood flow passageway.

In one embodiment there is provided an apparatus, wherein said control device controls said stimulation device to energize said electrical elements, such that electrical elements currently energized form at least one group of adjacent energized electrical elements.

In one embodiment there is provided an apparatus, wherein said elements in said group of energized electrical elements form a path of energized electrical elements.

In one embodiment there is provided an apparatus, wherein said path of energized electrical elements extends at least in part around the patient's erectile blood flow passageway, when said stimulation device is applied on the erectile blood flow passageway.

In one embodiment there is provided an apparatus, wherein said path of energized electrical elements extends completely around the patient's erectile blood flow passageway, when said stimulation device is applied on the erectile blood flow passageway.

In one embodiment there is provided an apparatus, wherein said elements in said group of energized electrical elements form two paths of energized electrical elements extending opposite to each other, when said stimulation device is applied on the patient's erectile blood flow passageway.

In one embodiment there is provided an apparatus, wherein said two paths of energized electrical elements extend on mutual sides of the patient's erectile blood flow passageway and at least substantially transverse to the direction of flow in the erectile blood flow passageway, when said stimulation device is applied on the erectile blood flow passageway.

In one embodiment there is provided an apparatus, wherein said electrical elements form a plurality of groups of elements, the groups forming a series of groups extending along the patient's erectile blood flow passageway in the direction of flow in the erectile blood flow passageway, when said stimulation device is applied on the erectile blood flow passageway.

In one embodiment the apparatus, comprises, in addition to a stimulation device, an implantable restriction device that engages the female erectile tissue or at least one venous blood vessel that drains the female erectile tissue and that is able to restrict the venous blood flow leaving the female erectile tissue. The restriction device may comprise a clamp or a loop and may be adjustable. The adjustment may be achieved with a hydraulic, mechanical, electrical or magnetic mean; or combinations thereof. The restriction device may be controlled, powered and energized in the same manner as the stimulation device and may be an integrated part of the system (se below).

In a second aspect there is provided a system comprising an apparatus as described above.

In one embodiment there is provided a system, further comprising at least one switch implantable in the patient for manually and non-invasively controlling the apparatus.

In one embodiment there is provided a system, further comprising a hydraulic device having an implantable hydraulic reservoir, which is hydraulically connected to the apparatus, wherein the apparatus is adapted to be non-invasively regulated by manually pressing the hydraulic reservoir.

In one embodiment there is provided a system, further comprising a wireless remote control for non-invasively controlling the apparatus.

In one embodiment there is provided a system, wherein the wireless remote control comprises at least one external signal transmitter and/or receiver, further comprising an internal signal receiver and/or transmitter implantable in the patient for receiving signals transmitted by the external signal transmitter or transmitting signals to the external signal receiver.

In one embodiment there is provided a system, wherein the wireless remote control transmits at least one wireless control signal for controlling the apparatus.

In one embodiment there is provided a system, wherein the wireless control signal comprises a frequency, amplitude, or phase modulated signal or a combination thereof.

In one embodiment there is provided a system, wherein the wireless remote control transmits an electromagnetic carrier wave signal for carrying the control signal.

In one embodiment there is provided a system, further comprising a wireless energy-transmission device for non-invasively energizing implantable energy consuming components of the apparatus or the system with wireless energy.

In one embodiment there is provided a system, wherein the wireless energy comprises a wave signal selected from the following: a sound wave signal, an ultrasound wave signal, an electromagnetic wave signal, an infrared light signal, a visible light signal, an ultra violet light signal, a laser light signal, a micro wave signal, a radio wave signal, an x-ray radiation signal and a gamma radiation signal.

In one embodiment there is provided a system, wherein the wireless energy comprises one of the following: an electric field, a magnetic field, a combined electric and magnetic field.

In one embodiment there is provided a system, wherein the control signal comprises one of the following: an electric field, a magnetic field, a combined electric and magnetic field.

In one embodiment there is provided a system, wherein the signal comprises an analogue signal, a digital signal, or a combination of an analogue and digital signal In one embodiment there is provided a system, further comprising an implantable internal energy source for powering implantable energy consuming components of the apparatus.

In one embodiment there is provided a system, further comprising an external energy source for transferring energy in a wireless mode, wherein the internal energy source is chargeable by the energy transferred in the wireless mode.

In one embodiment there is provided a system, further comprising a sensor or measuring device sensing or measuring a functional parameter correlated to the transfer of energy for charging the internal energy source, and a feedback device for sending feedback information from inside the patient's body to the outside thereof, the feedback information being related to the functional parameter sensed by the sensor or measured by the measuring device.

In one embodiment there is provided a system, further comprising a feedback device for sending feedback information from inside the patient's body to the outside thereof, the feedback information being related to at least one of a physiological parameter of the patient and a functional parameter related to the apparatus.

In one embodiment there is provided a system, further comprising a sensor and/or a measuring device and an implantable internal control unit for controlling the apparatus in response to information being related to at least one of a physiological parameter of the patient sensed by the sensor or measured by the measuring device and a functional parameter related to the apparatus sensed by the sensor or measured by the measuring device.

In one embodiment there is provided a system, wherein the physiological parameter is a pressure or motility.

In one embodiment there is provided a system, further comprising an external data communicator and an implantable internal data communicator communicating with the external data communicator, wherein the internal communicator feeds data related to the apparatus or the patient to the external data communicator and/or the external data communicator feeds data to the internal data communicator.

In one embodiment there is provided a system, further comprising an energy-transforming device for transforming the wireless energy transmitted by the energy-transmission device from a first form into a second form energy.

In one embodiment there is provided a system, wherein the energy-transforming device directly powers implantable energy consuming components of the apparatus with the second form energy, as the energy-transforming device transforms the first form energy transmitted by the energy-transmission device into the second form energy.

In one embodiment there is provided a system, wherein the second form energy comprises at least one of a direct current, pulsating direct current and an alternating current.

In one embodiment there is provided a system, further comprising an implantable accumulator, wherein the second form energy is used at least partly to charge the accumulator.

In one embodiment there is provided a system, wherein the energy of the first or second form comprises at least one of magnetic energy, kinetic energy, sound energy, chemical energy, radiant energy, electromagnetic energy, photo energy, nuclear energy thermal energy, non-magnetic energy, non-kinetic energy, non-chemical energy, non-sonic energy, non-nuclear energy and non-thermal energy.

In one embodiment there is provided a system, further comprising implantable electrical components including at least one voltage level guard and/or at least one constant current guard.

In one embodiment there is provided a system, further comprising a control device for controlling the transmission of wireless energy from the energy-transmission device, and an implantable internal energy receiver for receiving the transmitted wireless energy, the internal energy receiver being connected to implantable energy consuming components of the apparatus for directly or indirectly supplying received energy thereto, the system further comprising a determination device adapted to determine an energy balance between the energy received by the internal energy receiver and the energy used for the implantable energy consuming components of the apparatus, wherein the control device controls the transmission of wireless energy from the external energy-transmission device, based on the energy balance determined by the determination device.

In one embodiment there is provided a system, wherein the determination device is adapted to detect a change in the energy balance, and the control device controls the transmission of wireless energy based on the detected energy balance change.

In one embodiment there is provided a system, wherein the determination device is adapted to detect a difference between energy received by the internal energy receiver and energy used for the implantable energy consuming components of the apparatus, and the control device controls the transmission of wireless energy based on the detected energy difference.

In one embodiment there is provided a system, wherein the energy-transmission device comprises a coil placed externally to the human body, further comprising an implantable energy receiver to be placed internally in the human body and an electric circuit connected to power the external coil with electrical pulses to transmit the wireless energy, the electrical pulses having leading and trailing edges, the electric circuit adapted to vary first time intervals between successive leading and trailing edges and/or second time intervals between successive trailing and leading edges of the electrical pulses to vary the power of the transmitted wireless energy, the energy receiver receiving the transmitted wireless energy having a varied power.

In one embodiment there is provided a system, wherein the electric circuit is adapted to deliver the electrical pulses to remain unchanged except varying the first and/or second time intervals.

In one embodiment there is provided a system, wherein the electric circuit has a time constant and is adapted to vary the first and second time intervals only in the range of the first time constant, so that when the lengths of the first and/or second time intervals are varied, the transmitted power over the coil is varied.

In one embodiment there is provided a system, further comprising an implantable internal energy receiver for receiving wireless energy, the energy receiver having an internal first coil and a first electronic circuit connected to the first coil, and an external energy transmitter for transmitting wireless energy, the energy transmitter having an external second coil and a second electronic circuit connected to the second coil, wherein the external second coil of the energy transmitter transmits wireless energy which is received by the first coil of the energy receiver, the system further comprising a power switch for switching the connection of the internal first coil to the first electronic circuit on and off, such that feedback information related to the charging of the first coil is received by the external energy transmitter in the form of an impedance variation in the load of the external second coil, when the power switch switches the connection of the internal first coil to the first electronic circuit on and off.

In one embodiment there is provided a system, further comprising an implantable internal energy receiver for receiving wireless energy, the energy receiver having an internal first coil and a first electronic circuit connected to the first coil, and an external energy transmitter for transmitting wireless energy, the energy transmitter having an external second coil and a second electronic circuit connected to the second coil, wherein the external second coil of the energy transmitter transmits wireless energy which is received by the first coil of the energy receiver, the system further comprising a feedback device for communicating out the amount of energy received in the first coil as a feedback information, and wherein the second electronic circuit includes a determination device for receiving the feedback information and for comparing the amount of transferred energy by the second coil with the feedback information related to the amount of energy received in the first coil to obtain the coupling factors between the first and second coils.

In one embodiment there is provided a system, wherein the energy transmitter regulates the transmitted energy in response to the obtained coupling factor.

In one embodiment there is provided a system, wherein external second coil is adapted to be moved in relation to the internal first coil to establish the optimal placement of the second coil, in which the coupling factor is maximized.

In one embodiment there is provided a system, wherein the external second coil is adapted to calibrate the amount of transferred energy to achieve the feedback information in the determination device, before the coupling factor is maximized.

In addition, the stimulation device may comprise at least one elongated stimulation member adapted to form the stimulation member into at least a substantially closed loop around a portion of the female erectile tissue, the loop defining a stimulation opening, whereby the stimulation device is adapted to adjust the size of the stimulation opening.

In an alternative embodiment the apparatus may comprise a stimulation device adapted to increase the arterial blood flow reaching the female erectile tissue causing engorgement with blood of the female erectile tissue.

The stimulation device may comprise a heating member causing engorgement with blood of the female erectile tissue. Alternatively a muscle affecting the blood flow is stimulated.

In one embodiment a relaxation of said muscle may be achieved by excessive stimulation thereof.

Electric Stimulation

When stimulating female erectile tissue such as the corpus cavernosa or vestibular bulbs or venous blood vessels draining the female erectile tissue or muscular tissue affecting the blood flow leaving or arriving to the female erectile tissue or arterial blood vessels supplying blood to the female erectile tissue, an engorgement of said female erectile tissue occur. All the above is defined the erectile blood flow passageway.

In accordance with the present invention, the control device controls the stimulation device to intermittently stimulate different areas of the wall portion of the erectile blood flow passageway, such that at least two of the areas are stimulated at different points of time that is, the stimulation is shifted from one area to another area over time. Furthermore, the control device controls the stimulation device to stimulate each area during successive time periods, wherein each time period is short enough to maintain satisfactory blood circulation in the area until the lapse of the time period. This gives the advantage that the apparatus of the present invention enables continuous stimulation of the wall portion of the erectile blood flow passageway to achieve the desired flow control, while essentially maintaining over time the natural physiological properties of the erectile blood flow passageway without risking injuring the erectile blood flow passageway.

Also, by physiologically changing the places of stimulation on the erectile blood flow passageway over time as described above it is possible to create an advantageous changing stimulation pattern on the erectile blood flow passageway, in order to achieve a desired flow control.

The control device may control the stimulation device to stimulate one or more of the areas of the wall portion at a time, for example by sequentially stimulating the different areas. Furthermore, the control device may control the stimulation device to cyclically propagate the stimulation of the areas along the wall portion, preferably in accordance with a determined stimulation pattern. To achieve the desired reaction of the tissue wall of the erectile blood flow passageway during the stimulation thereof, the control device may control the stimulation device to, preferably cyclically, vary the intensity of the stimulation of the wall portion.

In a preferred embodiment of the invention, the control device controls the stimulation device to intermittently stimulate the areas of the wall portion with pulses that preferably form pulse trains. The pulse trains can be configured in many different ways. Thus, the control device may control the stimulation device to vary the amplitudes of the pulses of the pulse trains, the duty cycle of the individual pulses of each pulse train, the width of each pulse of the pulse trains, the length of each pulse train, the repetition frequency of the pulses of the pulse trains, the repetition frequency of the pulse trains, the number of pulses of each pulse train, and/or the off time periods between the pulse trains. Several pulse trains of different configurations may be employed to achieve the desired effect.

In case the control device controls the stimulation device to vary the off time periods between pulse trains that stimulate the respective area of the wall portion, it is also possible to control each off time period between pulse trains to last long enough to restore substantially normal blood circulation in the area when the latter is not stimulated during the off time periods.

In accordance with a preferred embodiment of the invention, the stimulation device is an electrically powered stimulation device that electrically stimulates the tissue wall portion of the erectile blood flow passageway, preferably with electric pulses.

Alternatively only the muscle tissue related to the blood flow in the erectile blood flow passageway may be stimulated. Over stimulation of muscle tissue may cause a relaxation of said tissue thus provoking engorgement of said rectile tissue. When talking about wall portion this includes also muscle tissue in any relevant position in this application.

The control device controls the stimulation device to stimulate the wall portion with electric pulses preferably in the form of electric pulse trains, to cause contraction of the wall portion. Of course, the configuration of the electric pulse trains may be similar to the above described pulse trains and the control device may control the stimulation device to electrically stimulate the different areas of the wall of the erectile blood flow passageway in the same manner as described above.

The electric stimulation device suitably comprises at least one, preferably a plurality of electrical elements, such as electrodes, for engaging and stimulating the wall portion with electric pulses. Optionally, the electrical elements may be are placed in a fixed orientation relative to one another. The control device controls the electric stimulation device to electrically energize the electrical elements, one at a time, or groups of electrical elements at a time. Preferably, the control device controls the electric stimulation device to cyclically energize each element with electric pulses. Optionally, the control device may control the stimulation device to energize the electrical elements, such that the electrical elements are energized one at a time in sequence, or such that a number or groups of the electrical elements are energized at the same time. Also, groups of electrical elements may be sequentially energized, either randomly or in accordance with a predetermined pattern.

The electrical elements may form any pattern of electrical elements. Preferably, the electrical elements form an elongate pattern of electrical elements, wherein the electrical elements are applicable on the patient's wall of the erectile blood flow passageway, such that the elongate pattern of electrical elements extends lengthwise along the wall of the erectile blood flow passageway, and the elements abut the respective areas of the wall portion. The elongate pattern of electrical elements may include one or more rows of electrical elements extending lengthwise along the wall of the erectile blood flow passageway. Each row of electrical elements may form a straight, helical or zig-zag path of electrical elements, or any form of path. The control device may control the stimulation device to successively energize the electrical elements longitudinally along the elongate pattern of electrical elements in a direction opposite to, or in the same direction as that of, the flow in the patient's rectile blood flow passageway.

Optionally, the control device may control the stimulation device to successively energize the electrical elements from a position substantially at the center of the constricted wall portion towards both ends of the elongate pattern of electrical elements. Where the lumen of the organ erectile blood flow passageway is to be kept closed for a relatively long time, the control device may control the stimulation device to energize the electrical elements, such that energized electrical elements form two waves of energized electrical elements that simultaneously advance from the center of the constricted wall portion in two opposite directions towards both ends of the elongate pattern of electrical elements. Such waves of energized electrical elements can be repeated over and over again without harming the erectile blood flow passageway and without moving blood in any direction in the erectile blood flow passageway.

The control device suitably controls the stimulation device to energize the electrical elements, such that the electrical elements currently energized form at least one group of adjacent energized electrical elements. In accordance with a first alternative, the elements in the group of energized electrical elements form one path of energized electrical elements. The path of energized electrical elements may extend at least in part around the patient's erectile blood flow passageways. In a second alternative, the elements of the group of energized electrical elements may form two paths of energized electrical elements extending on mutual sides of the patient's erectile blood flow passageway, preferably substantially transverse to the flow direction in the lumen of the erectile blood flow passageway. In a third alternative, the elements of the group of energized electrical elements may form more than two paths of energized electrical elements extending on different sides of the patient's erectile blood flow passageway, preferably substantially transverse to the flow direction in the patient's lumenerectile blood flow passageway.

In accordance with a preferred embodiment of the invention, the electrical elements form a plurality of groups of elements, wherein the groups form a series of groups extending along the patient's erectile blood flow passageway in the flow direction in the patient's lumenerectile blood flow passageway. The electrical elements of each group of electrical elements may form a path of elements extending at least in part around the patient's erectile blood flow passageway. In a first alternative, the electrical elements of each group of electrical elements may form more than two paths of elements extending on different sides of the patient's erectile blood flow passageway, preferably substantially transverse to the flow direction in the patient's lumenerectile blood flow passageway. The control device may control the stimulation device to energize the groups of electrical elements in the series of groups in random, or in accordance with a predetermined pattern.

Alternatively, the control device may control the stimulation device to successively energize the groups of electrical elements in the series of groups in a direction opposite to the flow in the patient's lumenerectile blood flow passageway, or in both said directions starting from a position substantially at the center of the constricted wall portion. For example, groups of energized electrical elements may form advancing waves of energized electrical elements, as described above; that is, the control device may control the stimulation device to energize the groups of electrical elements, such that energized electrical elements form two waves of energized electrical elements that simultaneously advance from the center of the constricted wall portion in two opposite directions towards both ends of the elongate pattern of electrical elements.

A structure may be provided for holding the electrical elements in a fixed orientation. Although the structure may be separate from the stimulation device, it is preferable that the structure is integrated in the stimulation device, which is a practical design and facilitates implantation of the stimulation devices. Where the electrical elements form an elongate pattern of electrical elements, the structure may be applicable on the patient's erectile blood flow passageway such that the elongate pattern of electrical elements extends along the erectile blood flow passageway in the same direction as that of the flow in the patient's lumenerectile blood flow passageway and the elements abut the respective areas of the wall portion of the erectile blood flow passageway.

Thermal Stimulation

In another embodiment of the invention, the stimulation device thermally stimulates the wall portion of the erectile blood flow passageway. Thus, the control device may control the stimulation device to cool the wall portion, when the wall portion is constricted, to cause contraction of the wall portion. For example, the control device may control the stimulation device to cool the constricted wall portion to cause contraction thereof, such that the flow in the lumen erectile blood flow passageway is at least further restricted, or further restricted but not stopped, or stopped. Alternatively, the control device may control the stimulation device to heat the arterial wall portion, when the wall portion is constricted and contracted, to cause expansion of the wall portion. Where the wall portion includes venous erectile blood flow passageway, the control device may control the stimulation device to cool the erectile blood flow passageway to cause contraction thereof, or heat the artierial erectile blood flow passageway to cause expansion thereof. Where applicable, thermal stimulation may be practised in any of the embodiments of the present invention, and the thermal stimulation may be controlled in response to various sensors, for example strain, motion or pressure sensors.

Sensor Controlled Stimulation Device

The apparatus may further comprising a control device for manually controlling the at least one stimulation device from outside the patients body, and may further comprise a control device for controlling the level of stimulation.

The apparatus preferable comprising a control device for adjusting the stimulation device to temporarily contract the female erectile tissue to restrict the blood flow leaving the female erectile tissue.

Alternatively the apparatus may comprise a control device and at least one sensor adapted to detect a physiological parameter of the patient and/or a functional parameter of the apparatus, wherein said control device comprises a control unit adapted to automatically control the at least one stimulation device based on input from said at least one sensor.

As mentioned above, the apparatus may comprise at least one implantable sensor, wherein the control device controls the constriction device and/or the stimulation device in response to signals from the sensor. Generally, the sensor directly or indirectly senses at least one physiological parameter of the patient, or at least one functional parameter of the apparatus, or at least one functional parameter of a medical implant in the patient.

Many different kinds of sensor for sensing physiological parameters may be used. For example pressure sensors for sensing pressure in the erectile blood flow passageway, strain sensors for sensing strain of the erectile blood flow passageway, flow sensors for sensing blood flow in the lumen of the erectile blood flow passageway, spectrophotometrical sensors, or sensors for sensing the distribution of the stimulation on the stimulated erectile blood flow passageway. Any conceivable sensors for sensing any other kind of useful physiological parameter may be used.

Many different kinds of sensors that sense functional parameters of the apparatus may also be used for the control of the stimulation device. For example sensors for sensing electric parameters of implanted electric components of the apparatus, or sensors for sensing the performance of implanted components of the apparatus. The sensor may comprise a pressure sensor for sensing as the physiological parameter a pressure in the patient's body that relates to the pressure in the erectile blood flow passageway of the patient's erectile blood flow passageway, wherein the control device controls stimulation device to change the constriction of the patient's wall portion of the erectile blood flow passageway in response to the pressure sensor sensing a predetermined value of measured pressure.

The above described sensors may be used in any of the embodiments of the invention, where applicable.

The control device may comprise an implantable internal control unit that directly controls the stimulation device in response to signals from the sensor. The control device may further comprise a wireless remote control adapted to set control parameters of the internal control unit from outside the patient without mechanically penetrating the patient. At least one of the control parameters, which is settable by the wireless remote control, is the physiological or functional parameter. Alternatively, the control device may comprise an external control unit outside the patient's body for controlling the stimulation device in response to signals from the sensor.

In a preferred embodiment, the system comprises at least one switch implantable in the patient for manually and non-invasively controlling the apparatus In another preferred embodiment, the system comprises a wireless remote control for non-invasively controlling the apparatus.

In a third aspect there is provided an operation method using an apparatus as described above, comprising the steps of:
  creating an opening in the skin or vaginal wall of the female patient
  dissecting at least one area of the female erectile tissue
  placing the stimulation device within said area, adapted to postoperatively stimulate said female erectile tissue on patient command.

In one embodiment there is provided an operation method, further comprising the step of controlling said stimulation device post-operatively and non-invasively from outside the body.

In one embodiment there is provided an operation method, further comprising the step of placing a power source within the body.

In one embodiment there is provided an operation method, wherein the step of placing a stimulation device comprises placing an integrated unit comprising the stimulation device and a power source in the same integrated unit.

In one embodiment there is provided an operation method, wherein the step of placing a power source comprises the step of placing a control unit and a rechargeable battery remote from the stimulation device.

In one embodiment there is provided an operation method, wherein the step of placing a stimulation device comprises placing electrodes and an electrical wire connected to a power source.

In one embodiment there is provided an operation method, wherein the step of creating an opening in the skin or vaginal wall of the female patient comprises:
  inserting a tube or needle into the patients body,
  filling the body through the tube or needle with a gas and thereby expanding a cavity within the female patients body,
  inserting at least two laparoscopic trocars into said cavity,
  inserting at least one camera trough at least one laparoscopic trocar, and
  inserting at least one dissecting tool through at least one laparoscopic trocar.

BRIEF DESCRIPTION OF THE DRAWINGS

The present invention will now be described in more detail by way of non-limiting embodiments and with reference to the accompanying drawings, in which:

FIGS. 2-16 schematically show various embodiments of the system for wirelessly powering the apparatus shown in FIG. 1.

DETAILED DESCRIPTION OF THE DRAWINGS

Figure 1A:
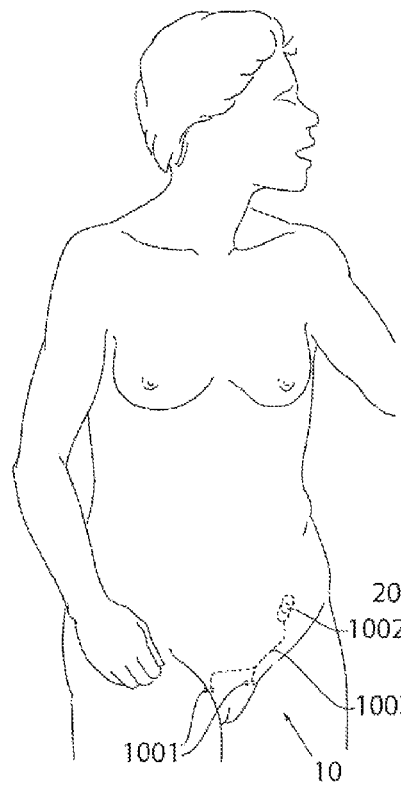
FIG. 1a schematically illustrates an apparatus and a system implanted in a female patient.

FIG. 1a is a schematic picture of patient having an apparatus 10 implanted, comprising a subcutaneously implanted control device 1002 and two stimulation devices 1001.

Figure 1B:
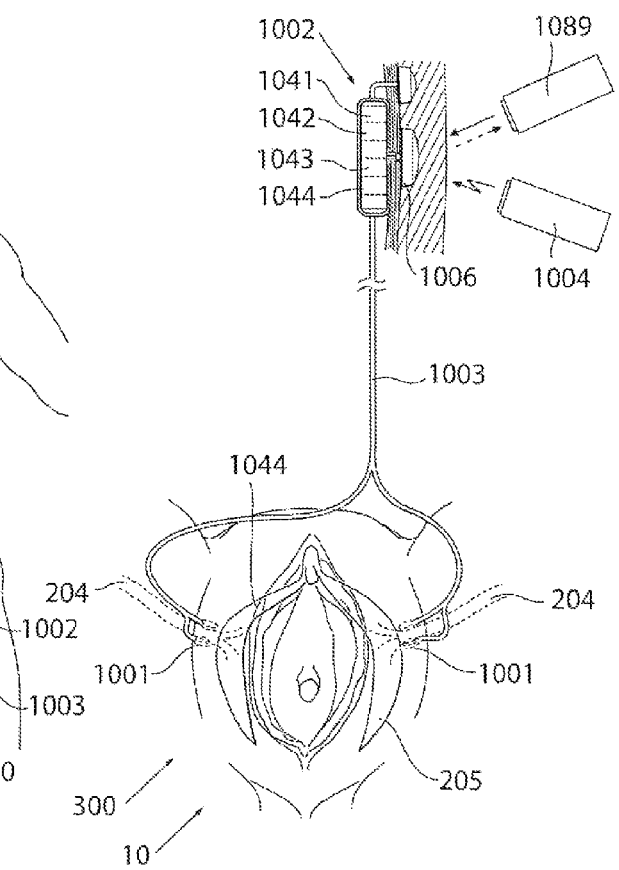
FIGS. 1b to 1d shows different embodiment of the sexual dysfunction apparatus and the system according to the invention.

FIG. 1b is a detailed illustration of the apparatus 10 and the system 300. The stimulation devices 1001, here illustrates as electrodes operable to stimulate the veins, is implanted to stimulate veins 204 of the female erectile tissue 205 of the patient. They are connected to the control device 1002 trough a power supply line 1003. An external energy-transmission device 1004 for energizing the apparatus transmits energy by at least one wireless energy signal. The system can be controlled with a remote control 1089. Also a subcutaneous control switch 1006 can be used to control the apparatus. In one embodiment a sensor 1044 measures at least one physiological or functional parameter. The location of the sensor 1044 is adapted to the circumstances, e.g. which parameter that should be measured. The control device 1002 can comprise at least one item selected from the group consisting of: an internal control unit 1041 for communication, an internal energy source 1042, a sensor control unit 1043, and an energy transforming device for transforming wireless energy from the energy transmission device 1004. If a non-rechargeable battery is used the energy-transforming device 1044 may be omitted but the other mentioned items may be used as suitable. In general, any item, or combinations of items, described and suited therefore, may be connected to the stimulation device and a sensor contacting the female organ via the connection line 1003. If e.g. the apparatus 10 is electrically operated it may be suitable to connect it to a source of electrical energy 1042 via the connection line 1003 which in this case may be an electrical conduit. The control unit 1041 may be connected to the source of electrical energy 1042.

Figure 1C:
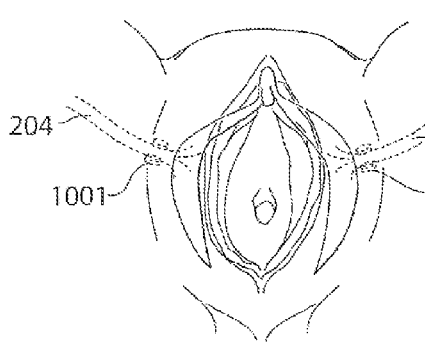

FIG. 1c shows two stimulation devices 1001 implanted as to engage veins of the corpora cavernosa. Other parts of the apparatus are not.

Figure 1D:
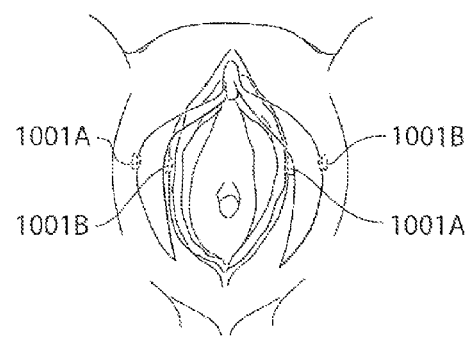

FIG. 1d demonstrates an alternative embodiment wherein the stimulation device is represented by different units 1001A and 1001B each operating on parts of the corpora cavernosa for its direct stimulation to obtain engorgement of the tissue.

FIG. 2 illustrates the system of FIG. 1 in the form of a more generalized block diagram showing the apparatus 10, the energy-transforming device 302 powering the apparatus 10 via power supply line 303, and the external energy-transmission device 304. The patient's skin 305, generally shown by a vertical line, separates the interior of the patient to the right of the line from the exterior to the left of the line. The implanted energy-transforming device 302 is adapted to supply energy consuming components of the apparatus with energy via a power supply line 303. An external energy-transmission device 304 for non-invasively energizing the apparatus 10 transmits energy by at least one wireless energy signal. The implanted energy-transforming device 302 transforms energy from the wireless energy signal into electric energy which is supplied via the power supply line 303.

The wireless energy signal may include a wave signal selected from the following: a sound wave signal, an ultrasound wave signal, an electromagnetic wave signal, an infrared light signal, a visible light signal, an ultra violet light signal, a laser light signal, a micro wave signal, a radio wave signal, an x-ray radiation signal and a gamma radiation signal. Alternatively, the wireless energy signal may include an electric or magnetic field, or a combined electric and magnetic field.

The wireless energy-transmission device 304 may transmit a carrier signal for carrying the wireless energy signal. Such a carrier signal may include digital, analogue or a combination of digital and analogue signals. In this case, the wireless energy signal includes an analogue or a digital signal, or a combination of an analogue and digital signal.

Generally speaking, the energy-transforming device 302 is provided for transforming wireless energy of a first form transmitted by the energy-transmission device 304 into energy of a second form, which typically is different from the energy of the first form. The implanted apparatus 10 is operable in response to the energy of the second form. The energy-transforming device 302 may directly power the apparatus with the second form energy, as the energy-transforming device 302 transforms the first form energy transmitted by the energy-transmission device 304 into the second form energy. The system may further include an implantable accumulator, wherein the second form energy is used at least partly to charge the accumulator.

Alternatively, the wireless energy transmitted by the energy-transmission device 304 may be used to directly power the apparatus, as the wireless energy is being transmitted by the energy-transmission device 304. Where the system comprises an operation device for operating the apparatus, as will be described below, the wireless energy transmitted by the energy-transmission device 304 may be used to directly power the operation device to create kinetic energy for the operation of the apparatus. The wireless energy of the first form may comprise sound waves and the energy-transforming device 302 may include a piezo-electric element for transforming the sound waves into electric energy. The energy of the second form may comprise electric energy in the form of a direct current or pulsating direct current, or a combination of a direct current and pulsating direct current, or an alternating current or a combination of a direct and alternating current. Normally, the apparatus comprises electric components that are energized with electrical energy. Other implantable electric components of the system may be at least one voltage level guard or at least one constant current guard connected with the electric components of the apparatus.

Optionally, one of the energy of the first form and the energy of the second form may comprise magnetic energy, kinetic energy, sound energy, chemical energy, radiant energy, electromagnetic energy, photo energy, nuclear energy or thermal energy. Preferably, one of the energy of the first form and the energy of the second form is non-magnetic, non-kinetic, non-chemical, non-sonic, non-nuclear or non-thermal.

The energy-transmission device may be controlled from outside the patient's body to release electromagnetic wireless energy, and the released electromagnetic wireless energy is used for operating the apparatus. Alternatively, the energy-transmission device is controlled from outside the patient's body to release non-magnetic wireless energy, and the released non-magnetic wireless energy is used for operating the apparatus.

The external energy-transmission device 304 also includes a wireless remote control having an external signal transmitter for transmitting a wireless control signal for non-invasively controlling the apparatus. The control signal is received by an implanted signal receiver which may be incorporated in the implanted energy-transforming device 302 or be separate there from.

The wireless control signal may include a frequency, amplitude, or phase modulated signal or a combination thereof. Alternatively, the wireless control signal includes an analogue or a digital signal, or a combination of an analogue and digital signal. Alternatively, the wireless control signal comprises an electric or magnetic field, or a combined electric and magnetic field.

The wireless remote control may transmit a carrier signal for carrying the wireless control signal. Such a carrier signal may include digital, analogue or a combination of digital and analogue signals. Where the control signal includes an analogue or a digital signal, or a combination of an analogue and digital signal, the wireless remote control preferably transmits an electromagnetic carrier wave signal for carrying the digital or analogue control signals.

FIG. 3 shows an embodiment of the invention identical to that of FIG. 2, except that a reversing device in the form of an electric switch 306 operable for example by polarized energy also is implanted in the patient for reversing the apparatus 10. When the switch is operated by polarized energy the wireless remote control of the external energy-transmission device 304 transmits a wireless signal that carries polarized energy and the implanted energy-transforming device 302 transforms the wireless polarized energy into a polarized current for operating the electric switch 306. When the polarity of the current is shifted by the implanted energy-transforming device 302 the electric switch 306 reverses the function performed by the apparatus 10.

FIG. 4 shows an embodiment of the invention identical to that of FIG. 2, except that an operation device 307 implanted in the patient for operating the apparatus 10 is provided between the implanted energy-transforming device 302 and the apparatus 10. This operation device can be in the form of a motor 307, such as an electric servomotor. The motor 307 is powered with energy from the implanted energy-transforming device 302, as the remote control of the external energy-transmission device 304 transmits a wireless signal to the receiver of the implanted energy-transforming device 302.

In all of these embodiments the energy-transforming device 302 may include a rechargeable accumulator like a battery or a capacitor to be charged by the wireless energy and supplies energy for any energy consuming part of the system.

As an alternative, the wireless remote control described above may be replaced by manual control of any implanted part to make contact with by the patient's hand most likely indirect, for example a press button placed under the skin.

FIG. 5 shows an embodiment of the invention identical to that of FIG. 2, except that it also comprises an operation device is in the form of an assembly 308 including a motor/pump unit 309 and a fluid reservoir 310 is implanted in the patient. In this case the apparatus 10 is hydraulically operated, i.e. hydraulic fluid is pumped by the motor/pump unit 309 from the fluid reservoir 310 through a conduit 311 to the apparatus 10 to operate the apparatus, and hydraulic fluid is pumped by the motor/pump unit 309 back from the apparatus 10 to the fluid reservoir 310 to return the apparatus to a starting position. The implanted energy-transforming device 398 transforms wireless energy into a current, for example a polarized current, for powering the motor/pump unit 309 via an electric power supply line 312.

Instead of a hydraulically operated apparatus 10, it is also envisaged that the operation device comprises a pneumatic operation device. In this case, the hydraulic fluid can be pressurized air to be used for regulation and the fluid reservoir is replaced by an air chamber.

In all of these embodiments the energy-transforming device 398 may include a rechargeable accumulator like a battery or a capacitor to be charged by the wireless energy and supplies energy for any energy consuming part of the system.

As an alternative, the wireless remote control described above may be replaced by manual control of any implanted part to make contact with by the patient's hand most likely indirect, for example a press button placed under the skin.

FIG. 6 shows an embodiment of the invention comprising the external energy-transmission device 304 with its wireless remote control, the apparatus 10, in this case hydraulically operated, and the implanted energy-transforming device 398, and further comprising a hydraulic fluid reservoir 313, a motor/pump unit 309 and an reversing device in the form of a hydraulic valve shifting device 314, all implanted in the patient. Of course the hydraulic operation could easily be performed by just changing the pumping direction and the hydraulic valve may therefore be omitted. The remote control may be a device separated from the external energy-transmission device or included in the same. The motor of the motor/pump unit 309 is an electric motor. In response to a control signal from the wireless remote control of the external energy-transmission device 304, the implanted energy-transforming device 398 powers the motor/pump unit 309 with energy from the energy carried by the control signal, whereby the motor/pump unit 309 distributes hydraulic fluid between the hydraulic fluid reservoir 313 and the apparatus 10. The remote control of the external energy-transmission device 304 controls the hydraulic valve shifting device 314 to shift the hydraulic fluid flow direction between one direction in which the fluid is pumped by the motor/pump unit 309 from the hydraulic fluid reservoir 313 to the apparatus 10 to operate the apparatus, and another opposite direction in which the fluid is pumped by the motor/pump unit 309 back from the apparatus 10 to the hydraulic fluid reservoir 313 to return the apparatus to a starting position.

FIG. 7 shows an embodiment of the invention comprising the external energy-transmission device 304 with its wireless remote control, the apparatus 10, the implanted energy-transforming device 302, an implanted internal control unit 315 controlled by the wireless remote control of the external energy-transmission device 304, an implanted accumulator 316 and an implanted capacitor 317. The internal control unit 315 arranges storage of electric energy received from the implanted energy-transforming device 302 in the accumulator 316, which supplies energy to the apparatus 10. In response to a control signal from the wireless remote control of the external energy-transmission device 304, the internal control unit 315 either releases electric energy from the accumulator 316 and transfers the released energy via power lines 318 and 319, or directly transfers electric energy from the implanted energy-transforming device 302 via a power line 320, the capacitor 317, which stabilizes the electric current, a power line 321 and the power line 319, for the operation of the apparatus 10.

The internal control unit is preferably programmable from outside the patient's body. In a preferred embodiment, the internal control unit is programmed to regulate the apparatus 10 according to a pre-programmed time-schedule or to input from any sensor sensing any possible physiological parameter of the patient or any functional parameter of the system.

Figure 10:
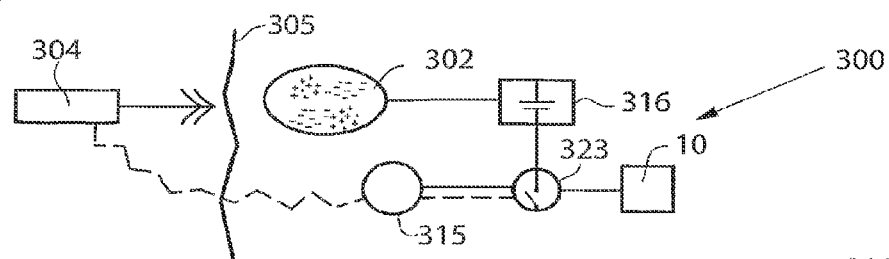

In accordance with an alternative, the capacitor 317 in the embodiment of FIG. 7 10 may be omitted. In accordance with another alternative, the accumulator 316 in this embodiment may be omitted.

FIG. 8 shows an embodiment of the invention identical to that of FIG. 2, except that a battery 322 for supplying energy for the operation of the apparatus 10 and an electric switch 323 for switching the operation of the apparatus 10 also are implanted in the patient. The electric switch 323 may be controlled by the remote control and may also be operated by the energy supplied by the implanted energy-transforming device 302 to switch from an off mode, in which the battery 322 is not in use, to an on mode, in which the battery 322 supplies energy for the operation of the apparatus 10.

FIG. 9 shows an embodiment of the invention identical to that of FIG. 8, except that an internal control unit 315 controllable by the wireless remote control of the external energy-transmission device 304 also is implanted in the patient. In this case, the electric switch 323 is operated by the energy supplied by the implanted energy-transforming device 302 to switch from an off mode, in which the wireless remote control is prevented from controlling the internal control unit 315 and the battery is not in use, to a standby mode, in which the remote control is permitted to control the internal control unit 315 to release electric energy from the battery 322 for the operation of the apparatus 10.

FIG. 10 shows an embodiment of the invention identical to that of FIG. 9, except that an accumulator 316 is substituted for the battery 322 and the implanted components are interconnected differently. In this case, the accumulator 316 stores energy from the implanted energy-transforming device 302. In response to a control signal from the wireless remote control of the external energy-transmission device 304, the internal control unit 315 controls the electric switch 323 to switch from an off mode, in which the accumulator 316 is not in use, to an on mode, in which the accumulator 316 supplies energy for the operation of the apparatus 10. The accumulator may be combined with or replaced by a capacitor.

Figure 11:
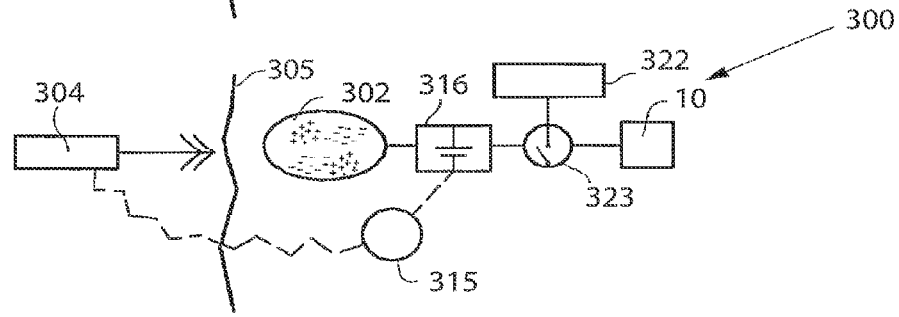

FIG. 11 shows an embodiment of the invention identical to that of FIG. 10, except that a battery 322 also is implanted in the patient and the implanted components are interconnected differently. In response to a control signal from the wireless remote control of the external energy-transmission device 304, the internal control unit 315 controls the accumulator 316 to deliver energy for operating the electric switch 323 to switch from an off mode, in which the battery 322 is not in use, to an on mode, in which the battery 322 supplies electric energy for the operation of the apparatus 10.

Alternatively, the electric switch 323 may be operated by energy supplied by the accumulator 316 to switch from an off mode, in which the wireless remote control is prevented from controlling the battery 322 to supply electric energy and is not in use, to a standby mode, in which the wireless remote control is permitted to control the battery 322 to supply electric energy for the operation of the apparatus 10.

It should be understood that the switch 323 and all other switches in this application should be interpreted in its broadest embodiment. This means a transistor, MCU, MCPU, ASIC, FPGA or a DA converter or any other electronic component or circuit that may switch the power on and off. Preferably the switch is controlled from outside the body, or alternatively by an implanted internal control unit.

Figure 12:
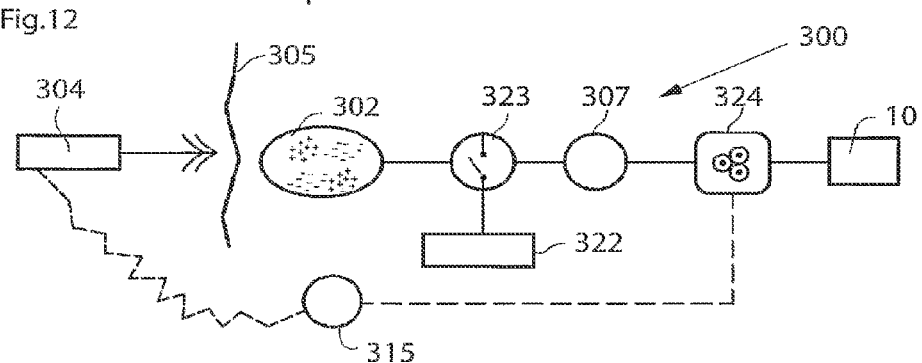

FIG. 12 shows an embodiment of the invention identical to that of FIG. 8, except that a motor 307, a mechanical reversing device in the form of a gear box 324, and an internal control unit 315 for controlling the gear box 324 also are implanted in the patient. The internal control unit 315 controls the gear box 324 to reverse the function performed by the apparatus 10 (mechanically operated). Even simpler is to switch the direction of the motor electronically. The gear box interpreted in its broadest embodiment may stand for a servo arrangement saving force for the operation device in favour of longer stroke to act.

Figure 13:
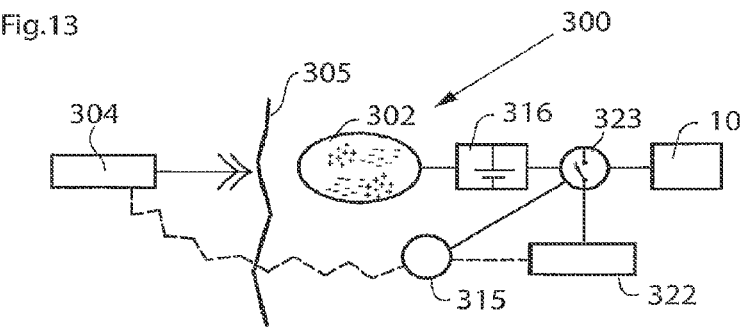
Figure 19:
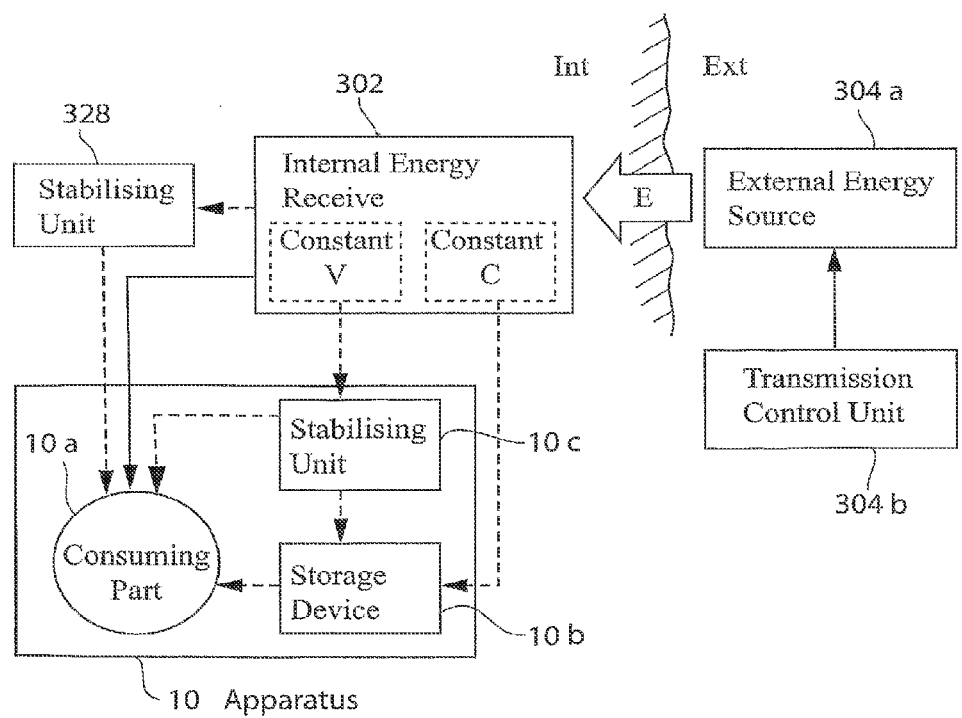
FIG. 19 is a more detailed block diagram of an arrangement for controlling the transmission of wireless energy used for the operation of the apparatus shown in FIG. 1.

FIG. 13 shows an embodiment of the invention identical to that of FIG. 19 except that the implanted components are interconnected differently. Thus, in this case the internal control unit 315 is powered by the battery 322 when the accumulator 316, suitably a capacitor, activates the electric switch 323 to switch to an on mode. When the electric switch 323 is in its on mode the internal control unit 315 is permitted to control the battery 322 to supply, or not supply, energy for the operation of the apparatus 10.

Figure 14:
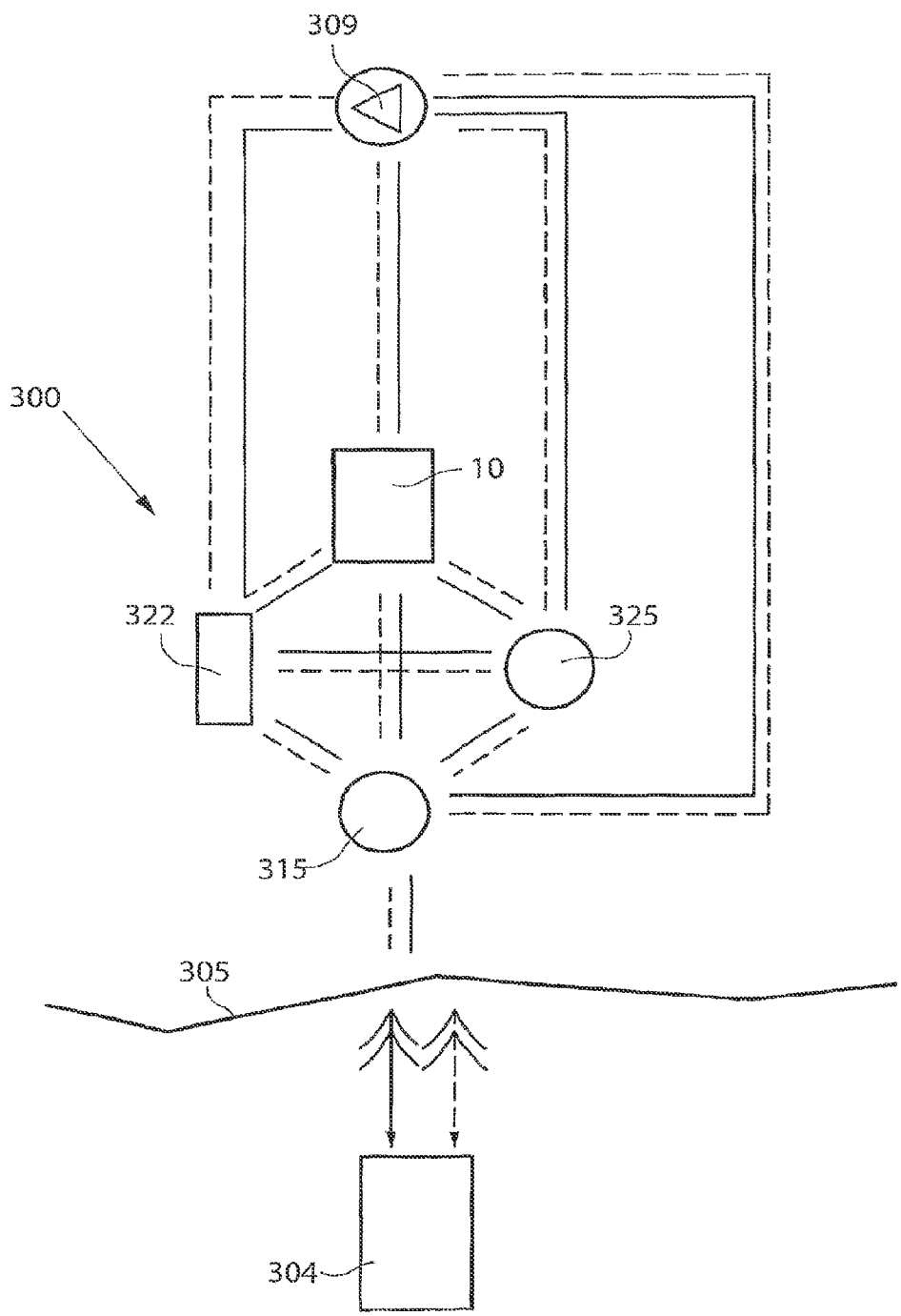

FIG. 14 schematically shows conceivable combinations of implanted components of the apparatus for achieving various communication options. Basically, there are the apparatus 10, the internal control unit 315, motor or pump unit 309, and the external energy-transmission device 304 including the external wireless remote control. As already described above the wireless remote control transmits a control signal which is received by the internal control unit 315, which in turn controls the various implanted components of the apparatus.

A feedback device, preferably comprising a sensor or measuring device 325, may be implanted in the patient for sensing a physiological parameter of the patient. The physiological parameter may be at least one selected from the group consisting of pressure, volume, diameter, stretching, elongation, extension, movement, bending, elasticity, muscle contraction, nerve impulse, body temperature, blood pressure, blood flow, heartbeats and breathing. The sensor may sense any of the above physiological parameters. For example, the sensor may be a pressure or motility sensor. Alternatively, the sensor 325 may be arranged to sense a functional parameter. The functional parameter may be correlated to the transfer of energy for charging an implanted energy source and may further include at least one selected from the group of parameters consisting of; electricity, any electrical parameter, pressure, volume, diameter, stretch, elongation, extension, movement, bending, elasticity, temperature and flow.

The feedback may be sent to the internal control unit or out to an external control unit preferably via the internal control unit. Feedback may be sent out from the body via the energy transfer system or a separate communication system with receiver and transmitters. The internal control unit 315, or alternatively the external wireless remote control of the external energy-transmission device 304, may control the apparatus 10 in response to signals from the sensor 325. A transceiver may be combined with the sensor 325 for sending information on the sensed physiological parameter to the external wireless remote control. The wireless remote control may comprise a signal transmitter or transceiver and the internal control unit 315 may comprise a signal receiver or transceiver. Alternatively, the wireless remote control may comprise a signal receiver or transceiver and the internal control unit 315 may comprise a signal transmitter or transceiver. The above transceivers, transmitters and receivers may be used for sending information or data related to the apparatus 10 from inside the patient's body to the outside thereof. Where the motor/pump unit 309 and battery 322 for powering the motor/pump unit 309 are implanted, information related to the charging of the battery 322 may be fed back. To be more precise, when charging a battery or accumulator with energy feedback information related to said charging process is sent and the energy supply is changed accordingly.

Figure 15:
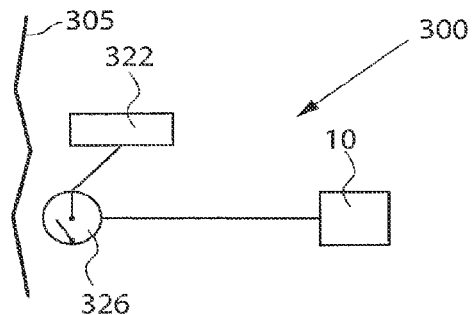

FIG. 15 shows an alternative embodiment wherein the apparatus 10 is regulated from outside the patient's body. The system 300 comprises a battery 322 connected to the apparatus 10 via a subcutaneous electric switch 326. Thus, the regulation of the apparatus 10 is performed non-invasively by manually pressing the subcutaneous switch, whereby the operation of the apparatus 10 is switched on and off. It will be appreciated that the shown embodiment is a simplification and that additional components, such as an internal control unit or any other part disclosed in the present application can be added to the system. Two subcutaneous switches may also be used. In the preferred embodiment one implanted switch sends information to the internal control unit to perform a certain predetermined performance and when the patient press the switch again the performance is reversed.

Figure 16:
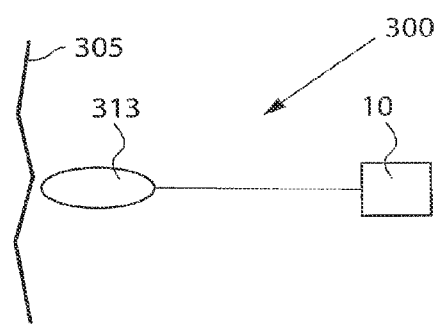

FIG. 16 shows an alternative embodiment, wherein the system 300 comprises a hydraulic fluid reservoir 313 hydraulically connected to the apparatus. Non-invasive regulation is performed by manually pressing the hydraulic reservoir connected to the apparatus.

The system may include an external data communicator and an implantable internal data communicator communicating with the external data communicator. The internal communicator feeds data related to the apparatus or the patient to the external data communicator and/or the external data communicator feeds data to the internal data communicator.

Figure 17:
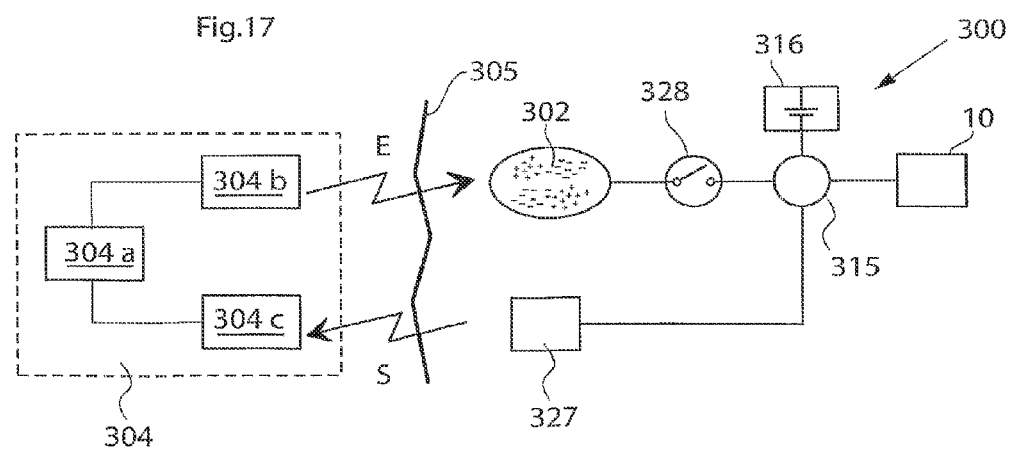
FIG. 17 is a schematic block diagram illustrating an arrangement for supplying an accurate amount of energy used for the operation of the apparatus shown in FIG. 1.

FIG. 17 schematically illustrates an arrangement of the system that is capable of sending information from inside the patient's body to the outside thereof to give feedback information related to at least one functional parameter of the apparatus or system, or related to a physiological parameter of the patient, in order to supply an accurate amount of energy to an implanted internal energy receiver 302 connected to implanted energy consuming components of the apparatus 10. Such an energy receiver 302 may include an energy source and/or an energy-transforming device. Briefly described, wireless energy is transmitted from an external energy source 304a located outside the patient and is received by the internal energy receiver 302 located inside the patient. The internal energy receiver is adapted to directly or indirectly supply received energy to the energy consuming components of the apparatus 10 via a switch 326. An energy balance is determined between the energy received by the internal energy receiver 302 and the energy used for the apparatus 10, and the transmission of wireless energy is then controlled based on the determined energy balance. The energy balance thus provides an accurate indication of the correct amount of energy needed, which is sufficient to operate the apparatus 10 properly, but without causing undue temperature rise.

In FIG. 17 the patient's skin is indicated by a vertical line 305. Here, the energy receiver comprises an energy-transforming device 302 located inside the patient, preferably just beneath the patient's skin 305. Generally speaking, the implanted energy-transforming device 302 may be placed in the abdomen, thorax, muscle fascia (e.g. in the abdominal wall), subcutaneously, or at any other suitable location. The implanted energy-transforming device 302 is adapted to receive wireless energy E transmitted from the external energy-source 304a provided in an external energy-transmission device 304 located outside the patient's skin 305 in the vicinity of the implanted energy-transforming device 302.

As is well known in the art, the wireless energy E may generally be transferred by means of any suitable Transcutaneous Energy Transfer (TET) device, such as a device including a primary coil arranged in the external energy source 304a and an adjacent secondary coil arranged in the implanted energy-transforming device 302. When an electric current is fed through the primary coil, energy in the form of a voltage is induced in the secondary coil which can be used to power the implanted energy consuming components of the apparatus, e.g. after storing the incoming energy in an implanted energy source, such as a rechargeable battery or a capacitor. However, the present invention is generally not limited to any particular energy transfer technique, TET devices or energy sources, and any kind of wireless energy may be used.

The amount of energy received by the implanted energy receiver may be compared with the energy used by the implanted components of the apparatus. The term "energy used" is then understood to include also energy stored by implanted components of the apparatus. A control device includes an external control unit 304b that controls the external energy source 304a based on the determined energy balance to regulate the amount of transferred energy. In order to transfer the correct amount of energy, the energy balance and the required amount of energy is determined by means of a determination device including an implanted internal control unit 315 connected between the switch 326 and the apparatus 10. The internal control unit 315 may thus be arranged to receive various measurements obtained by suitable sensors or the like, not shown, measuring certain characteristics of the apparatus 10, somehow reflecting the required amount of energy needed for proper operation of the apparatus 10. Moreover, the current condition of the patient may also be detected by means of suitable measuring devices or sensors, in order to provide parameters reflecting the patient's condition. Hence, such characteristics and/or parameters may be related to the current state of the apparatus 10, such as power consumption, operational mode and temperature, as well as the patient's condition reflected by parameters such as; body temperature, blood pressure, heartbeats and breathing. Other kinds of physiological parameters of the patient and functional parameters of the device are described elsewhere.

Furthermore, an energy source in the form of an accumulator 316 may optionally be connected to the implanted energy-transforming device 302 via the control unit 315 for accumulating received energy for later use by the apparatus 10. Alternatively or additionally, characteristics of such an accumulator, also reflecting the required amount of energy, may be measured as well. The accumulator may be replaced by a rechargeable battery, and the measured characteristics may be related to the current state of the battery, any electrical parameter such as energy consumption voltage, temperature, etc. In order to provide sufficient voltage and current to the apparatus 10, and also to avoid excessive heating, it is clearly understood that the battery should be charged optimally by receiving a correct amount of energy from the implanted energy-transforming device 302, i.e. not too little or too much. The accumulator may also be a capacitor with corresponding characteristics.

For example, battery characteristics may be measured on a regular basis to determine the current state of the battery, which then may be stored as state information in a suitable storage means in the internal control unit 315. Thus, whenever new measurements are made, the stored battery state information can be updated accordingly. In this way, the state of the battery can be "calibrated" by transferring a correct amount of energy, so as to maintain the battery in an optimal condition.

Thus, the internal control unit 315 of the determination device is adapted to determine the energy balance and/or the currently required amount of energy, (either energy per time unit or accumulated energy) based on measurements made by the above-mentioned sensors or measuring devices of the apparatus 10, or the patient, or an implanted energy source if used, or any combination thereof. The internal control unit 315 is further connected to an internal signal transmitter 327, arranged to transmit a control signal reflecting the determined required amount of energy, to an external signal receiver 304c connected to the external control unit 304b. The amount of energy transmitted from the external energy source 304a may then be regulated in response to the received control signal. Alternatively, the determination device may include the external control unit 304b. In this alternative, sensor measurements can be transmitted directly to the external control unit 304b wherein the energy balance and/or the currently required amount of energy can be determined by the external control unit 304b, thus integrating the above-described function of the internal control unit 315 in the external control unit 304b. In that case, the internal control unit 315 can be omitted and the sensor measurements are supplied directly to the internal signal transmitter 327 which sends the measurements over to the external signal receiver 304c and the external control unit 304b. The energy balance and the currently required amount of energy can then be determined by the external control unit 304b based on those sensor measurements. Hence, the present solution according to the arrangement of FIG. 17 employs the feed back of information indicating the required energy, which is more efficient than previous solutions because it is based on the actual use of energy that is compared to the received energy, e.g. with respect to the amount of energy, the energy difference, or the energy receiving rate as compared to the energy rate used by implanted energy consuming components of the apparatus. The apparatus may use the received energy either for consuming or for storing the energy in an implanted energy source or the like. The different parameters discussed above would thus be used if relevant and needed and then as a tool for determining the actual energy balance. However, such parameters may also be needed per se for any actions taken internally to specifically operate the apparatus.

The internal signal transmitter 327 and the external signal receiver 304c may be implemented as separate units using suitable signal transfer means, such as radio, IR (Infrared) or ultrasonic signals. Alternatively, the internal signal transmitter 327 and the external signal receiver 304c may be integrated in the implanted energy-transforming device 302 and the external energy source 304a, respectively, so as to convey control signals in a reverse direction relative to the energy transfer, basically using the same transmission technique. The control signals may be modulated with respect to frequency, phase or amplitude.

Thus, the feedback information may be transferred either by a separate communication system including receivers and transmitters or may be integrated in the energy system. In accordance with the present invention, such an integrated information feedback and energy system comprises an implantable internal energy receiver for receiving wireless energy, the energy receiver having an internal first coil and a first electronic circuit connected to the first coil, and an external energy transmitter for transmitting wireless energy, the energy transmitter having an external second coil and a second electronic circuit connected to the second coil. The external second coil of the energy transmitter transmits wireless energy which is received by the first coil of the energy receiver. This system further comprises a power switch for switching the connection of the internal first coil to the first electronic circuit on and off, such that feedback information related to the charging of the first coil is received by the external energy transmitter in the form of an impedance variation in the load of the external second coil, when the power switch switches the connection of the internal first coil to the first electronic circuit on and off. In implementing this system in the arrangement of FIG. 17, the switch 326 is either separate and controlled by the internal control unit 315, or integrated in the internal control unit 315. It should be understood that the switch 326 should be interpreted in its broadest embodiment. This means a transistor, MCU, MCPU, ASIC FPGA or a DA converter or any other electronic component or circuit that may switch the power on and off.

To conclude, the energy supply arrangement illustrated in FIG. 17 may operate basically in the following manner. The energy balance is first determined by the internal control unit 315 of the determination device. A control signal reflecting the required amount of energy is also created by the internal control unit 315, and the control signal is transmitted from the internal signal transmitter 327 to the external signal receiver 304c. Alternatively, the energy balance can be determined by the external control unit 304b instead depending on the implementation, as mentioned above. In that case, the control signal may carry measurement results from various sensors. The amount of energy emitted from the external energy source 304a can then be regulated by the external control unit 304b, based on the determined energy balance, e.g. in response to the received control signal. This process may be repeated intermittently at certain intervals during ongoing energy transfer, or may be executed on a more or less continuous basis during the energy transfer.

The amount of transferred energy can generally be regulated by adjusting various transmission parameters in the external energy source 304a, such as voltage, current, amplitude, wave frequency and pulse characteristics.

This system may also be used to obtain information about the coupling factors between the coils in a TET system even to calibrate the system both to find an optimal place for the external coil in relation to the internal coil and to optimize energy transfer. Simply comparing in this case the amount of energy transferred with the amount of energy received. For example if the external coil is moved the coupling factor may vary and correctly displayed movements could cause the external coil to find the optimal place for energy transfer. Preferably, the external coil is adapted to calibrate the amount of transferred energy to achieve the feedback information in the determination device, before the coupling factor is maximized.

This coupling factor information may also be used as a feedback during energy transfer. In such a case, the energy system of the present invention comprises an implantable internal energy receiver for receiving wireless energy, the energy receiver having an internal first coil and a first electronic circuit connected to the first coil, and an external energy transmitter for transmitting wireless energy, the energy transmitter having an external second coil and a second electronic circuit connected to the second coil. The external second coil of the energy transmitter transmits wireless energy which is received by the first coil of the energy receiver. This system further comprises a feedback device for communicating out the amount of energy received in the first coil as a feedback information, and wherein the second electronic circuit includes a determination device for receiving the feedback information and for comparing the amount of transferred energy by the second coil with the feedback information related to the amount of energy received in the first coil to obtain the coupling factor between the first and second coils. The energy transmitter may regulate the transmitted energy in response to the obtained coupling factor.

Figure 18:
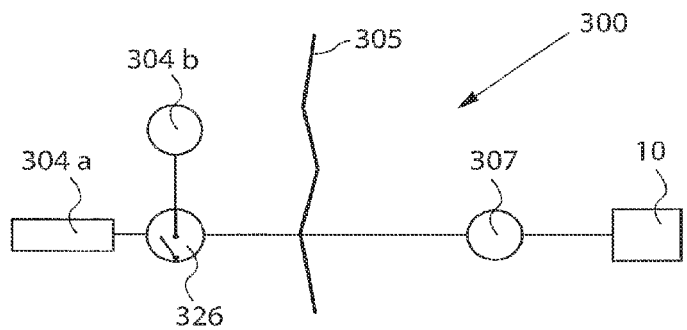
FIG. 18 schematically shows an embodiment of the system, in which the apparatus is operated with wire bound energy.

With reference to FIG. 18, although wireless transfer of energy for operating the apparatus has been described above to enable non-invasive operation, it will be appreciated that the apparatus can be operated with wire bound energy as well. Such an example is shown in FIG. 18, wherein an external switch 326 is interconnected between the external energy source 304a and an operation device, such as an electric motor 307 operating the apparatus 10. An external control unit 304b controls the operation of the external switch 326 to effect proper operation of the apparatus 10.

FIG. 19 illustrates different embodiments for how received energy can be supplied to and used by the apparatus 10. Similar to the example of FIG. 17, an internal energy receiver 302 receives wireless energy E from an external energy source 304a which is controlled by a transmission control unit 304b. The internal energy receiver 302 may comprise a constant voltage circuit, indicated as a dashed box "constant V" in the figure, for supplying energy at constant voltage to the apparatus 10. The internal energy receiver 302 may further comprise a constant current circuit, indicated as a dashed box "constant C" in the figure, for supplying energy at constant current to the apparatus 10.

The apparatus 10 comprises an energy consuming part 10a, which may be a motor, pump, restriction device, or any other medical appliance that requires energy for its electrical operation. The apparatus 10 may further comprise an energy storage device 10b for storing energy supplied from the internal energy receiver 302. Thus, the supplied energy may be directly consumed by the energy consuming part 10a, or stored by the energy storage device 10b, or the supplied energy may be partly consumed and partly stored. The apparatus 10 may further comprise an energy stabilizing unit 10c for stabilizing the energy supplied from the internal energy receiver 302. Thus, the energy may be supplied in a fluctuating manner such that it may be necessary to stabilize the energy before consumed or stored.

The energy supplied from the internal energy receiver 302 may further be accumulated and/or stabilized by a separate energy stabilizing unit 328 located outside the apparatus 10, before being consumed and/or stored by the apparatus 10. Alternatively, the energy stabilizing unit 328 may be integrated in the internal energy receiver 302. In either case, the energy stabilizing unit 328 may comprise a constant voltage circuit and/or a constant current circuit.

It should be noted that FIG. 17 and FIG. 19 illustrate some possible but non-limiting implementation options regarding how the various shown functional components and elements can be arranged and connected to each other. However, the skilled person will readily appreciate that many variations and modifications can be made within the scope of the present invention.

Figure 20:
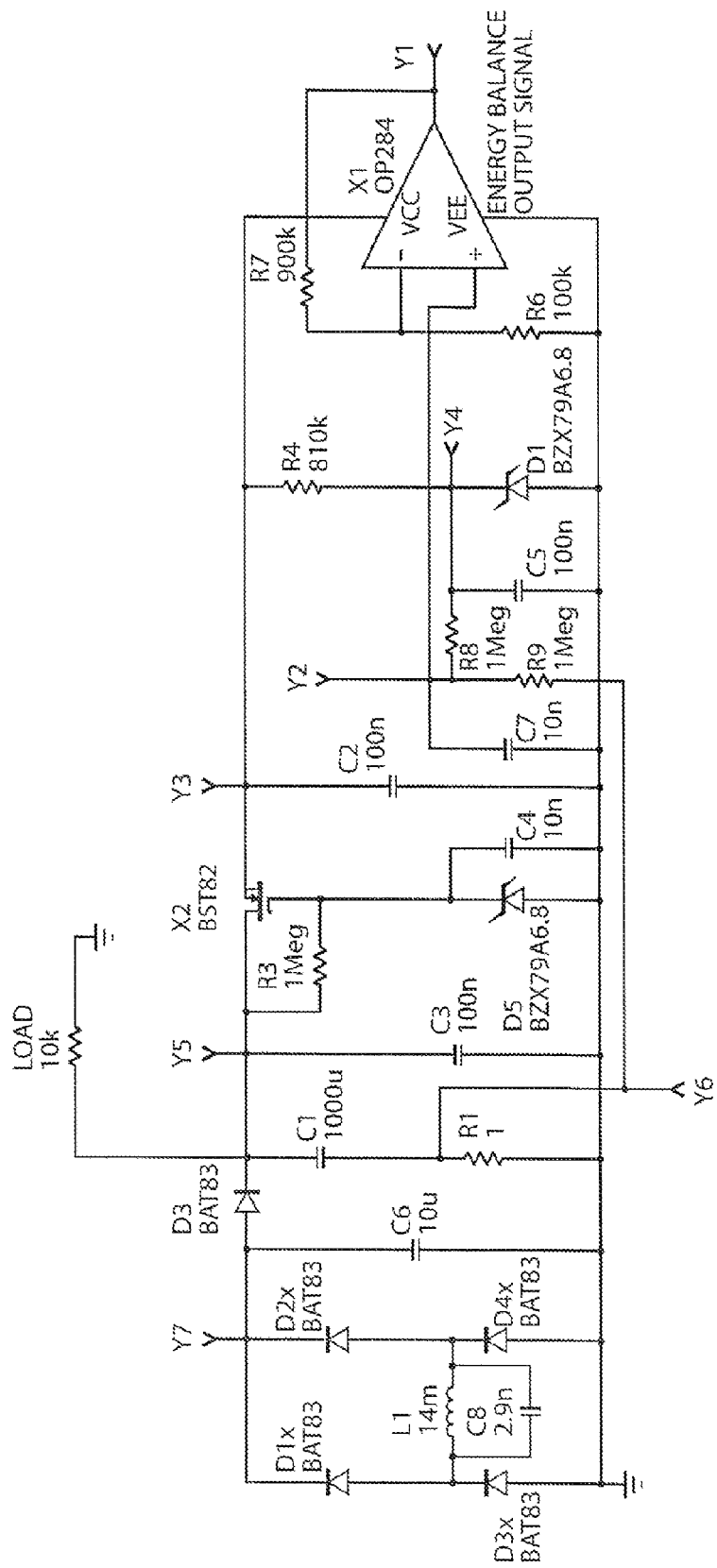
FIG. 20 is a circuit for the arrangement shown in FIG. 19, according to a possible implementation example.

FIG. 20 schematically shows an energy balance measuring circuit of one of the proposed designs of the system for controlling transmission of wireless energy, or energy balance control system. The circuit has an output signal centered on 2.5V and proportionally related to the energy imbalance. The derivative of this signal shows if the value goes up and down and how fast such a change takes place. If the amount of received energy is lower than the energy used by implanted components of the apparatus, more energy is transferred and thus charged into the energy source. The output signal from the circuit is typically feed to an A/D converter and converted into a digital format. The digital information can then be sent to the external energy-transmission device allowing it to adjust the level of the transmitted energy. Another possibility is to have a completely analog system that uses comparators comparing the energy balance level with certain maximum and minimum thresholds sending information to external energy-transmission device if the balance drifts out of the max/min window.

The schematic FIG. 20 shows a circuit implementation for a system that transfers energy to the implanted energy components of the apparatus of the present invention from outside of the patient's body using inductive energy transfer. An inductive energy transfer system typically uses an external transmitting coil and an internal receiving coil. The receiving coil, L1, is included in the schematic FIG. 3; the transmitting parts of the system are excluded.

The implementation of the general concept of energy balance and the way the information is transmitted to the external energy transmitter can of course be implemented in numerous different ways. The schematic FIG. 20 and the above described method of evaluating and transmitting the information should only be regarded as examples of how to implement the control system.

Circuit Details

In FIG. 20 the symbols Y1, Y2, Y3 and so on symbolize test points within the circuit. The components in the diagram and their respective values are values that work in this particular implementation which of course is only one of an infinite number of possible design solutions.

Energy to power the circuit is received by the energy receiving coil L1. Energy to implanted components is transmitted in this particular case at a frequency of 25 kHz. The energy balance output signal is present at test point Y1.

Those skilled in the art will realize that the above various embodiments of the system could be combined in many different ways. For example, the electric switch 306 of FIG. 3 could be incorporated in any of the embodiments of FIGS. 6-12, the hydraulic valve shifting device 314 of FIG. 6 could be incorporated in the embodiment of FIG. 5, and the gear box 324 could be incorporated in the embodiment of FIG. 4. Please observe that the switch simply could mean any electronic circuit or component. The embodiments described in connection with FIGS. 17, 19 and 20 identify a method and a system for controlling transmission of wireless energy to implanted energy consuming components of an electrically operable apparatus. Such a method and system will be defined in general terms in the following.

A method is thus provided for controlling transmission of wireless energy supplied to implanted energy consuming components of an apparatus as described above. The wireless energy E is transmitted from an external energy source located outside the patient and is received by an internal energy receiver located inside the patient, the internal energy receiver being connected to the implanted energy consuming components of the apparatus for directly or indirectly supplying received energy thereto. An energy balance is determined between the energy received by the internal energy receiver and the energy used for the apparatus. The transmission of wireless energy E from the external energy source is then controlled based on the determined energy balance.

The wireless energy may be transmitted inductively from a primary coil in the external energy source to a secondary coil in the internal energy receiver. A change in the energy balance may be detected to control the transmission of wireless energy based on the detected energy balance change. A difference may also be detected between energy received by the internal energy receiver and energy used for the medical device, to control the transmission of wireless energy based on the detected energy difference.

When controlling the energy transmission, the amount of transmitted wireless energy may be decreased if the detected energy balance change implies that the energy balance is increasing, or vice versa. The decrease/increase of energy transmission may further correspond to a detected change rate.

The amount of transmitted wireless energy may further be decreased if the detected energy difference implies that the received energy is greater than the used energy, or vice versa. The decrease/increase of energy transmission may then correspond to the magnitude of the detected energy difference.

As mentioned above, the energy used for the medical device may be consumed to operate the medical device, and/or stored in at least one energy storage device of the medical device.

When electrical and/or physiological parameters of the medical device and/or physiological parameters of the patient are determined, the energy may be transmitted for consumption and storage according to a transmission rate per time unit which is determined based on said parameters. The total amount of transmitted energy may also be determined based on said parameters.

When a difference is detected between the total amount of energy received by the internal energy receiver and the total amount of consumed and/or stored energy, and the detected difference is related to the integral over time of at least one measured electrical parameter related to said energy balance, the integral may be determined for a monitored voltage and/or current related to the energy balance.

When the derivative is determined over time of a measured electrical parameter related to the amount of consumed and/or stored energy, the derivative may be determined for a monitored voltage and/or current related to the energy balance.

The transmission of wireless energy from the external energy source may be controlled by applying to the external energy source electrical pulses from a first electric circuit to transmit the wireless energy, the electrical pulses having leading and trailing edges, varying the lengths of first time intervals between successive leading and trailing edges of the electrical pulses and/or the lengths of second time intervals between successive trailing and leading edges of the electrical pulses, and transmitting wireless energy, the transmitted energy generated from the electrical pulses having a varied power, the varying of the power depending on the lengths of the first and/or second time intervals.

In that case, the frequency of the electrical pulses may be substantially constant when varying the first and/or second time intervals. When applying electrical pulses, the electrical pulses may remain unchanged, except for varying the first and/or second time intervals. The amplitude of the electrical pulses may be substantially constant when varying the first and/or second time intervals. Further, the electrical pulses may be varied by only varying the lengths of first time intervals between successive leading and trailing edges of the electrical pulses.

A train of two or more electrical pulses may be supplied in a row, wherein when applying the train of pulses, the train having a first electrical pulse at the start of the pulse train and having a second electrical pulse at the end of the pulse train, two or more pulse trains may be supplied in a row, wherein the lengths of the second time intervals between successive trailing edge of the second electrical pulse in a first pulse train and leading edge of the first electrical pulse of a second pulse train are varied.

When applying the electrical pulses, the electrical pulses may have a substantially constant current and a substantially constant voltage. The electrical pulses may also have a substantially constant current and a substantially constant voltage. Further, the electrical pulses may also have a substantially constant frequency. The electrical pulses within a pulse train may likewise have a substantially constant frequency.

The circuit formed by the first electric circuit and the external energy source may have a first characteristic time period or first time constant, and when effectively varying the transmitted energy, such frequency time period may be in the range of the first characteristic time period or time constant or shorter.

A system comprising an apparatus as described above is thus also provided for controlling transmission of wireless energy supplied to implanted energy consuming components of the apparatus. In its broadest sense, the system comprises a control device for controlling the transmission of wireless energy from an energy-transmission device, and an implantable internal energy receiver for receiving the transmitted wireless energy, the internal energy receiver being connected to implantable energy consuming components of the apparatus for directly or indirectly supplying received energy thereto. The system further comprises a determination device adapted to determine an energy balance between the energy received by the internal energy receiver and the energy used for the implantable energy consuming components of the apparatus, wherein the control device controls the transmission of wireless energy from the external energy-transmission device, based on the energy balance determined by the determination device.

Further, the system may comprise any of the following:
- A primary coil in the external energy source adapted to transmit the wireless energy inductively to a secondary coil in the internal energy receiver.
- The determination device is adapted to detect a change in the energy balance, and the control device controls the transmission of wireless energy based on the detected energy balance change
- The determination device is adapted to detect a difference between energy received by the internal energy receiver and energy used for the implantable energy consuming components of the apparatus, and the control device controls the transmission of wireless energy based on the detected energy difference.
- The control device controls the external energy-transmission device to decrease the amount of transmitted wireless energy if the detected energy balance change implies that the energy balance is increasing, or vice versa, wherein the decrease/increase of energy transmission corresponds to a detected change rate.
- The control device controls the external energy-transmission device to decrease the amount of transmitted wireless energy if the detected energy difference implies that the received energy is greater than the used energy, or vice versa, wherein the decrease/increase of energy transmission corresponds to the magnitude of said detected energy difference.
- The energy used for the apparatus is consumed to operate the apparatus, and/or stored in at least one energy storage device of the apparatus.
- Where electrical and/or physiological parameters of the apparatus and/or physiological parameters of the patient are determined, the energy-transmission device transmits the energy for consumption and storage according to a transmission rate per time unit which is determined by the determination device based on said parameters. The determination device also determines the total amount of transmitted energy based on said parameters.

When a difference is detected between the total amount of energy received by the internal energy receiver and the total amount of consumed and/or stored energy, and the detected difference is related to the integral over time of at least one measured electrical parameter related to the energy balance, the determination device determines the integral for a monitored voltage and/or current related to the energy balance.

When the derivative is determined over time of a measured electrical parameter related to the amount of consumed and/or stored energy, the determination device determines the derivative for a monitored voltage and/or current related to the energy balance.

The energy-transmission device comprises a coil placed externally to the human body, and an electric circuit is provided to power the external coil with electrical pulses to transmit the wireless energy. The electrical pulses have leading and trailing edges, and the electric circuit is adapted to vary first time intervals between successive leading and trailing edges and/or second time intervals between successive trailing and leading edges of the electrical pulses to vary the power of the transmitted wireless energy. As a result, the energy receiver receiving the transmitted wireless energy has a varied power.

The electric circuit is adapted to deliver the electrical pulses to remain unchanged except varying the first and/or second time intervals.

The electric circuit has a time constant and is adapted to vary the first and second time intervals only in the range of the first time constant, so that when the lengths of the first and/or second time intervals are varied, the transmitted power over the coil is varied.

The electric circuit is adapted to deliver the electrical pulses to be varied by only varying the lengths of first time intervals between successive leading and trailing edges of the electrical pulses.

The electric circuit is adapted to supplying a train of two or more electrical pulses in a row, said train having a first electrical pulse at the start of the pulse train and having a second electrical pulse at the end of the pulse train, and the lengths of the second time intervals between successive trailing edge of the second electrical pulse in a first pulse train and leading edge of the first electrical pulse of a second pulse train are varied by the first electronic circuit.

The electric circuit is adapted to provide the electrical pulses as pulses having a substantially constant height and/or amplitude and/or intensity and/or voltage and/or current and/or frequency.

The electric circuit has a time constant, and is adapted to vary the first and second time intervals only in the range of the first time constant, so that when the lengths of the first and/or second time intervals are varied, the transmitted power over the first coil are varied.

The electric circuit is adapted to provide the electrical pulses varying the lengths of the first and/or the second time intervals only within a range that includes the first time constant or that is located relatively close to the first time constant, compared to the magnitude of the first time constant.

FIGS. 21-24 show in more detail block diagrams of four different ways of hydraulically or pneumatically powering an implanted apparatus according to the invention.

Figure 21:
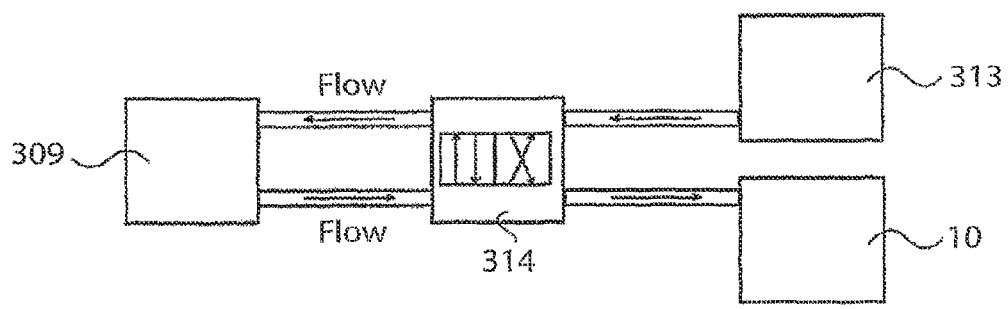
FIGS. 21-27C show various ways of arranging hydraulic or pneumatic powering of an apparatus implanted in a patient.

FIG. 21 shows a system as described above with. The system comprises an implanted apparatus 10 and further a separate regulation reservoir 313, a one way pump 309 and an alternate valve 314.

Figure 22:
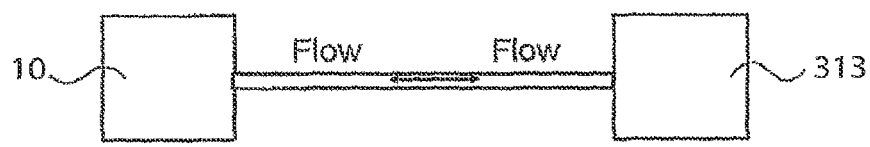

FIG. 22 shows the apparatus 10 and a fluid reservoir 313. By moving the wall of the regulation reservoir or changing the size of the same in any other different way, the adjustment of the apparatus may be performed without any valve, just free passage of fluid any time by moving the reservoir wall.

Figure 23:
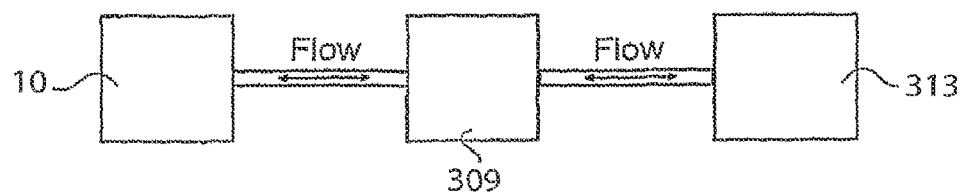

FIG. 23 shows the apparatus 10, a two way pump 309 and the regulation reservoir 313.

Figure 24:
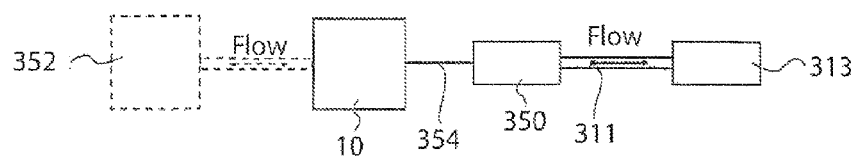

FIG. 24 shows a block diagram of a reversed servo system with a first closed system controlling a second closed system. The servo system comprises a regulation reservoir 313 and a servo reservoir 350. The servo reservoir 350 mechanically controls an implanted apparatus 10 via a mechanical interconnection 354. The apparatus has an expandable/contactable cavity. This cavity is preferably expanded or contracted by supplying hydraulic fluid from the larger adjustable reservoir 352 in fluid connection with the apparatus 10. Alternatively, the cavity contains compressible gas, which can be compressed and expanded under the control of the servo reservoir 350.

The servo reservoir 350 can also be part of the apparatus itself.

Figure 25A:
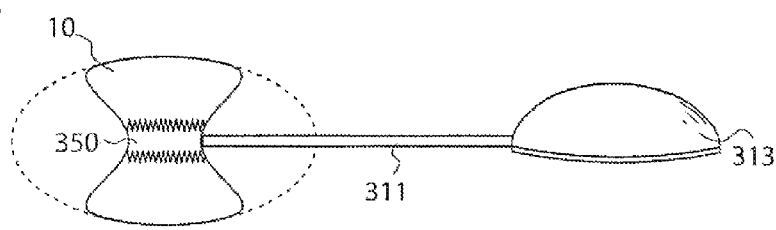
Figure 25B:
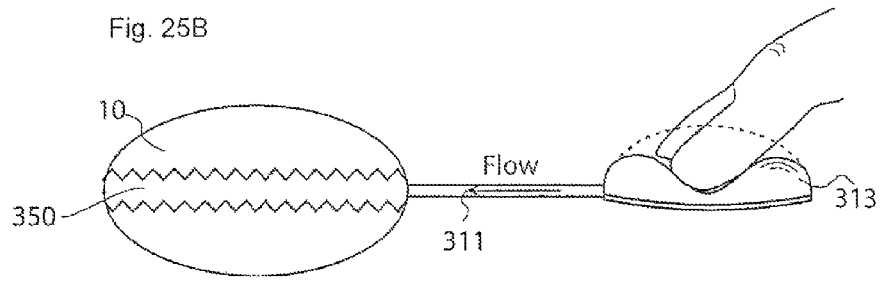
Figure 25C:
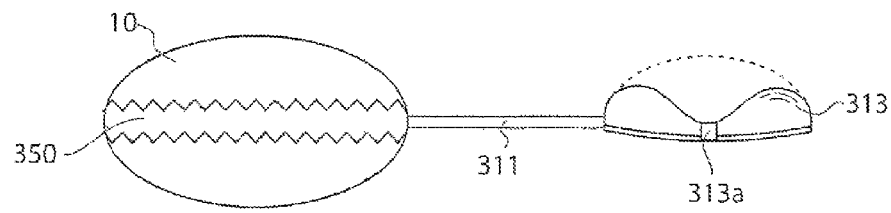
Figure 26:
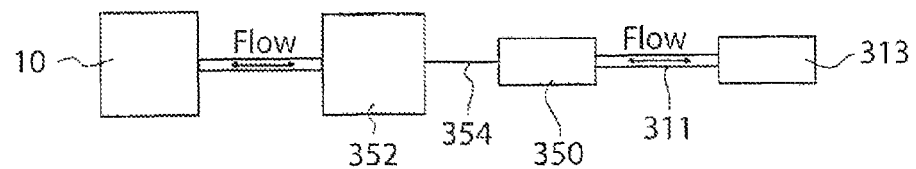

In one embodiment, the regulation reservoir is placed subcutaneous under the patient's skin and is operated by pushing the outer surface thereof by means of a finger. This system is illustrated in FIGS. 25a-c. In FIG. 25a, a flexible subcutaneous regulation reservoir 313 is shown connected to a bulge shaped servo reservoir 350 by means of a conduit 311. This bellow shaped servo reservoir 350 is comprised in a flexible apparatus 10. In the state shown in FIG. 25a, the servo reservoir 350 contains a minimum of fluid and most fluid is found in the regulation reservoir 313. Due to the mechanical interconnection between the servo reservoir 350 and the apparatus 10, the outer shape of the apparatus 10 is contracted, i.e., it occupies less than its maximum volume. This maximum volume is shown with dashed lines in the figure.

FIG. 25b shows a state wherein a user, such as the patient in with the apparatus is implanted, presses the regulation reservoir 313 so that fluid contained therein is brought to flow through the conduit 311 and into the servo reservoir 350, which, thanks to its bellow shape, expands longitudinally. This expansion in turn expands the apparatus 10 so that it occupies its maximum volume.

The regulation reservoir 313 is preferably provided with means 313a for keeping its shape after compression. This means, which is schematically shown in the figure, will thus keep the apparatus 10 in a stretched position also when the user releases the regulation reservoir. In this way, the regulation reservoir essentially operates as an on/off switch for the system.

An alternative embodiment of hydraulic or pneumatic operation will now be described with reference to FIGS. 26 and 27a-c. The block diagram shown in FIG. 26 comprises with a first closed system controlling a second closed system. The first system comprises a regulation reservoir 313 and a servo reservoir 350. The servo reservoir 350 mechanically controls a larger adjustable reservoir 352 via a mechanical interconnection 354. An implanted apparatus 10 having an expandable/contactable cavity is in turn controlled by the larger adjustable reservoir 352 by supply of hydraulic fluid from the larger adjustable reservoir 352 in fluid connection with the apparatus 10.

Figure 27A:
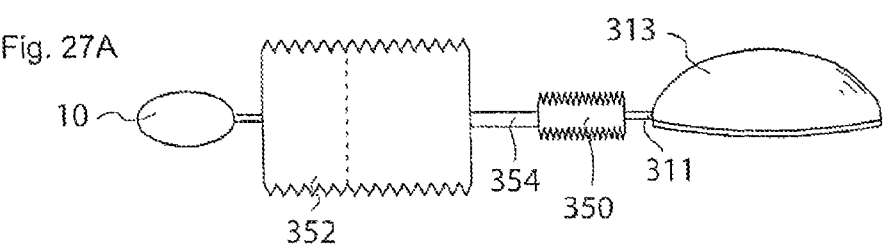
Figure 27B:
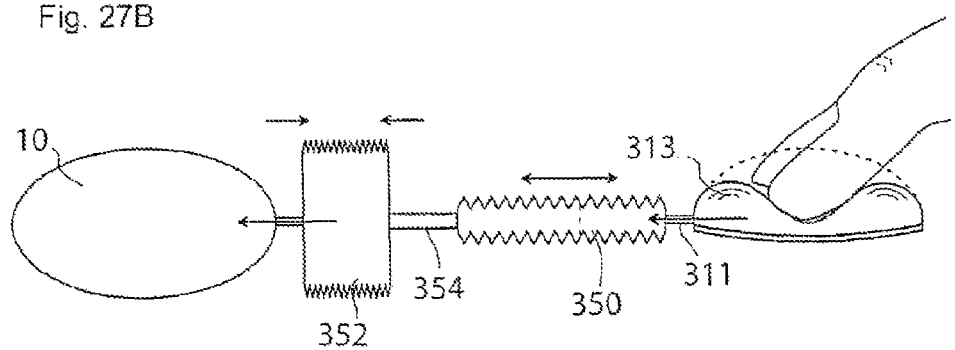
Figure 27C:
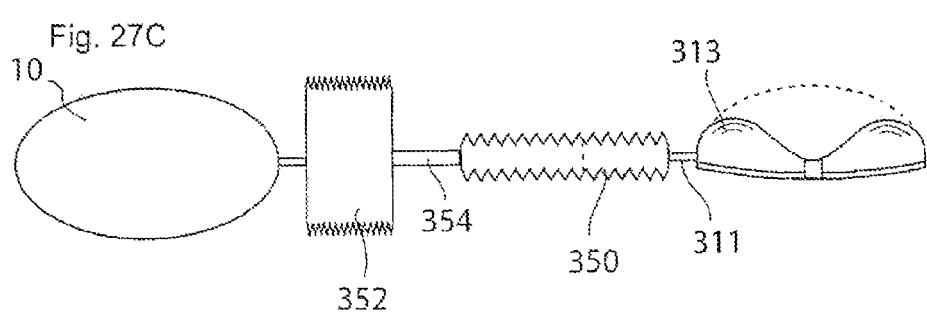

An example of this embodiment will now be described with reference to FIG. 27a-c. Like in the previous embodiment, the regulation reservoir is placed subcutaneous under the patient's skin and is operated by pushing the outer surface thereof by means of a finger. The regulation reservoir 313 is in fluid connection with a bellow shaped servo reservoir 350 by means of a conduit 311. In the first closed system 313, 311, 350 shown in FIG. 27a, the servo reservoir 350 contains a minimum of fluid and most fluid is found in the regulation reservoir 313.

The servo reservoir 350 is mechanically connected to a larger adjustable reservoir 352, in this example also having a bellow shape but with a larger diameter than the servo reservoir 350. The larger adjustable reservoir 352 is in fluid connection with the apparatus 10. This means that when a user pushes the regulation reservoir 313, thereby displacing fluid from the regulation reservoir 313 to the servo reservoir 350, the expansion of the servo reservoir 350 will displace a larger volume of fluid from the larger adjustable reservoir 352 to the apparatus 10. In other words, in this reversed servo, a small volume in the regulation reservoir is compressed with a higher force and this creates a movement of a larger total area with less force per area unit.

Like in the previous embodiment described above with reference to FIGS. 25a-c, the regulation reservoir 313 is preferably provided with means 313a (FIG. 27c) for keeping its shape after compression. This means, which is schematically shown in the figure, will thus keep the apparatus 10 in a stretched position also when the user releases the regulation reservoir. In this way, the regulation reservoir essentially operates as an on/off switch for the system.

Other features and uses of the invention and their associated advantages will be evident to a person skilled in the art upon reading the description.

It is to be understood that this invention is not limited to the particular embodiments shown here. The scope of the present invention is limited only by the appended claims and equivalents thereof.

The invention claimed is:

1. A method for treating, operating, or heating and operating, a female patient with an apparatus or a system including the apparatus, comprising a stimulation device adapted to indirect stimulate an erectile blood flow passageway to increase the amount of blood in the female erectile tissue and thereby obtaining engorgement with blood of the female erectile tissue by indirect affecting said erectile blood flow passageway,
the stimulation device is further adapted to stimulate a muscle related to arterial blood flow reaching the female erectile tissue, adapted to stimulate the muscle enough to relax the muscle to thereby cause relaxation of said muscle, to thereby increase the arterial blood flow, thereby obtaining said engorgement with blood of the female erectile tissue, wherein the method comprising the steps of,
stimulating using said apparatus or said system including said apparatus
stimulating the muscle enough to thereby cause relaxation of said muscle, resulting in increasing the arterial blood flow, thereby obtaining said engorgement with blood of the female erectile tissue.

2. The method according to claim 1, comprising the steps of:
creating an opening in the skin or vaginal wall of the female patient:
dissecting at least one area of the female erectile tissue; and
placing the stimulation device within said area, adapted to postoperatively stimulate said female erectile tissue on patient command.

3. The method according to claim 2, wherein the step of creating an opening in the skin or vaginal wall of the female patient comprises:
inserting a tube or needle into the patient's body,
filling the body through the tube or needle with a gas and thereby expanding a cavity within the female patient's body,
inserting at least two laparo-or endoscopic trocars into said cavity,
inserting at least one camera through at least one trocar,
inserting at least one dissecting tool through at least one trocar.

4. The method according to claim 1, wherein the steps of stimulating is used for controlling said stimulation device during an operation.

5. The method according to claim 2, wherein the step of placing the stimulation device, comprising the step of placing a power source within the body.

6. The method according to claim 5, wherein the step of placing a stimulation device comprises placing an integrated unit comprising the stimulation device with the power source in the same integrated unit.

7. The method according to claim 5, wherein the step of placing a power source comprises the step of placing a control unit and a rechargeable battery remote from the stimulation device.

8. The method according to claim 5, wherein the step of placing a stimulation device comprises placing electrical electrodes in the patient and an electrical wire connecting the electrodes to a power source.

9. The method according to claim 1, comprising the additional step of controlling said stimulation device post-operatively and non-invasively from outside the body.

10. The method according to claim 3, comprising the additional operational step of placing a power source within the body.

11. The method according to claim 10, wherein the step of placing a stimulation device comprises placing an integrated unit comprising the stimulation device with the power source in the same integrated unit.

12. The method according to claim 10, wherein the step of placing a power source comprises the step of placing a control unit and a rechargeable battery remote from the stimulation device.

13. The method according to claim 3, wherein the step of placing a stimulation device comprises placing electrical electrodes in the patient and an electrical wire connecting the electrodes to a power source.

14. The method according to claim 1, comprising the steps of, on the patient command,
stimulating indirect the erectile blood flow passageway to increase the amount of blood in the female erectile tissue and thereby obtaining engorgement with blood of the female erectile tissue, when at least one of;
using a wireless remote control, for non-invasively controlling the apparatus, and
using at least one switch implanted in the patient for manually and non-invasively controlling the apparatus.

15. The method according to claim 1, comprising the step of controlling the level of stimulation using
a control device.

16. The method according to claim 1, comprising the steps of;
setting control parameters of an internal control unit from outside the patient's body non-invasively;
setting at least one physiological or functional parameter.

17. The method according to claim 1, wherein the apparatus comprise a control device and at least one sensor adapted to detect a physiological parameter of the patient and/or a functional parameter of the apparatus, wherein the method further comprising the steps of;
controlling by the control device the stimulation device in response to signals from the sensor,
controlling automatically the stimulation device based on input from said at least one sensor.

18. The method according to claim 1, wherein the apparatus comprising at least one of the following at least one sensor; pressure sensor for sensing pressure in the erectile blood flow passageway, strain sensor for sensing strain of the erectile blood flow passageway, flow sensor for sensing blood flow in the lumen of the erectile blood flow passageway, spectrophoto-metrical sensor, or sensor for sensing the distribution of the stimulation on the stimulated erectile blood flow passageway, sensor for sensing electric parameters of any implanted electric components of the apparatus, sensor for sensing the performance of implanted components of the apparatus, and a sensor for sensing any useful physiological parameter.

19. The method according to claim 1, comprising the steps of;
sensing by a pressure sensor a physiological parameter being a pressure in the patient's body that relates to the pressure in the erectile blood flow passageway of the patient's erectile blood flow passageway.
controlling by a control device the stimulation device to change the erectile blood flow passageway in response to the pressure sensor sensing a predetermined value of measured pressure.

20. The method according to claim 17, further comprising controlling directly, by at least one of;
an implantable internal control unit being part of a control device, the stimulation device in response to signals from the sensor;
an external unit placed outside the patient's body being part of a control device, the stimulation device in response to signals from the sensor.

* * * * *